(12) United States Patent
Østensen et al.

(10) Patent No.: US 12,745,921 B2
(45) Date of Patent: Sep. 29, 2026

(54) MANGANESE-ENHANCED MAGNETIC RESONANCE IMAGING

(71) Applicant: IC Targets AS, Oslo (NO)

(72) Inventors: Jonny Østensen, Oslo (NO); Willy Eidsaunet, Kløfta (NO)

(73) Assignee: IC Targets AS, Oslo (NO)

( * ) Notice: Subject to any disclaimer, the term of this patent is extended or adjusted under 35 U.S.C. 154(b) by 347 days.

(21) Appl. No.: 18/566,924

(22) PCT Filed: Jun. 3, 2022

(86) PCT No.: PCT/EP2022/065181
§ 371 (c)(1),
(2) Date: Dec. 4, 2023

(87) PCT Pub. No.: WO2022/258517
PCT Pub. Date: Dec. 15, 2022

(65) Prior Publication Data
US 2024/0277246 A1 Aug. 22, 2024

(30) Foreign Application Priority Data
Jun. 7, 2021 (NO) .................................. 20210734

(51) Int. Cl.
*A61B 5/055* (2006.01)
*A61B 5/00* (2006.01)
*A61B 5/145* (2006.01)
*A61K 49/10* (2006.01)
(Continued)

(52) U.S. Cl.
CPC ............ *A61B 5/055* (2013.01); *A61B 5/0044* (2013.01); *A61B 5/14535* (2013.01);
(Continued)

(58) Field of Classification Search
CPC ... A61B 5/055; A61B 5/0044; A61B 5/14535; A61B 5/4866; G01R 33/50; G01R 33/5601; G01R 33/56366
See application file for complete search history.

(56) References Cited

U.S. PATENT DOCUMENTS 8,738,114 B2 * 5/2014 Hu ......................... A61B 5/055 600/420
2010/0166667 A1 * 7/2010 Jynge ................... A61K 49/103 424/9.3

FOREIGN PATENT DOCUMENTS

WO 2010/093635 A2 8/2010

OTHER PUBLICATIONS

Rocklage, S. et al., "Manganese(II) N,N'-Dipyridoxylethylenediamine-N,iV'-diacetate 5,5/-Bis(phosphate). Synthesis and Characterization of a Paramagnetic Chelate for Magnetic Resonance Imaging Enhancement", Inorg. Chem., 28, pp. 477-485, Feb. 1989.
(Continued)

*Primary Examiner* — Chu Chuan Liu
(74) *Attorney, Agent, or Firm* — F. Brent Nix, Esq.; Johnson, Marcou, Isaacs & Nix, LLC; Drew P. Harding

(57) ABSTRACT

The present invention relates to manganese-enhanced MRI, more specifically to a method for determining a cardiomyocyte cellular manganese uptake rate of a subject, contrast agent comprising a manganese contrast agent, or a pharmaceutically acceptable salt thereof, for use in a method for in vivo diagnosis of heart disease in a subject, a computer-implemented method of determining a cardiomyocyte cellular manganese uptake rate in a subject, a data processing apparatus comprising means for carrying out said computer-implemented method, a computer program comprising instructions which, when the program is executed by a computer, cause the computer to carry out said computer-
(Continued)

implemented method, and a computer-readable medium having stored thereon said computer program.

17 Claims, 7 Drawing Sheets

(51) Int. Cl.
*G01R 33/50* (2006.01)
*G01R 33/56* (2006.01)
*G01R 33/563* (2006.01)

(52) U.S. Cl.
CPC ............ *A61K 49/106* (2013.01); *G01R 33/50* (2013.01); *G01R 33/5601* (2013.01); *G01R 33/56366* (2013.01)

(56) References Cited

OTHER PUBLICATIONS

Spath, et al., "Manganese-enhanced magnetic resonance imaging in dilated cardiomyopathy and hypertrophic cardiomyopathy", European Heart Journal—Cardiovascular Imaging, 22, pp. 1463-1472, 2021.

Spath, et al., "Supplementary Material—Manganese-enhanced magnetic resonance imaging in dilated cardiomyopathy and hypertrophic cardiomyopathy", European Heart Journal—Cardiovascular Imaging, 8 pages, 2020.

Skjold, et al., "An Apparent Unidirectional Influx Constant for Manganese as a Measure of Myocardial Calcium Channel Activity", Journal of Magnetic Resonance Imaging, 24, pp. 1047-1055, 2006.

IC Targets AS, International Search Report for PCT/EP2022/065181, 4 pages, Sep. 21, 2022.

IC Targets AS, Norwegian Search Report for No. 20210734, 2 pages, Jan. 3, 2022.

Yamada, A. et al., "Comprehensive assessments of myocardial tissue kinetic parameters of K1, k2, MBF, lambda and ECV by using a synergistic quantitative analysis of first-pass myocardial perfusion MRI and pre-and post-contrast T1 mapping in patients with myocardial infarction", retrieved from http://submissions.mirasmart.com/ISMRM2016/ViewSubmission.aspx?sbmID=2061&validate=false> [Accessed Dec. 17, 2021] 2 pages, May 2016.

* cited by examiner

MANGANESE-ENHANCED MAGNETIC RESONANCE IMAGING

FIELD OF THE INVENTION

The present invention relates to manganese-enhanced MRI, more specifically to a method for determining the cardiomyocyte cellular manganese uptake rate of a subject, contrast agent comprising a manganese contrast agent, or a pharmaceutically acceptable salt thereof, for use in a method for in vivo diagnosis of heart disease in a subject, a computer-implemented method of determining a cardiomyocyte cellular manganese uptake rate in a subject, a data processing apparatus comprising means for carrying out said computer-implemented method, a computer program comprising instructions which, when the program is executed by a computer, cause the computer to carry out said computer-implemented method, and a computer-readable medium having stored thereon said computer program.

BACKGROUND OF THE INVENTION

Cardiovascular MRI is an essential tool in the diagnosis of a range of cardiovascular diseases, routinely being used for quantification of myocardial volumes, mass and function, and increasingly also valvular heart disease. With its high paramagnetic moment, manganese—in the form of $Mn^{2+}$ ions—was one of the first MRI contrast agents assessed in humans. Manganese-enhanced MRI (MEMRI) directly provides intracellular contrast of viable myocardium and has over the last 40 years emerged as a useful intracellular myocardial contrast imaging method that can identify functional myocardium. Myocardial MEMRI relies upon two important properties of the $Mn^{2+}$ ion:

- the ion enters cells, such as cardiomyocytes, via L-type calcium channels to accumulate in the cell in proportion to the L-type channel activity, and
- the ion is paramagnetic, increasing the longitudinal relaxation rate R1 and reducing the longitudinal relaxation time (T1) of tissues, hence functioning as an excellent T1 contrast agent (Eq. 1).

$$\Delta R1 = \Delta\frac{1}{T1} \quad \text{(Eq. 1)}$$

Unchelated manganese is mainly bound to proteins, but in steady state with a low concentration free manganese enters the cardiomyocytes through the L-type calcium channels. Unlike $Ca^{2+}$, which has a significant redistribution between intracellular and extracellular compartments during the course of each heartbeat, $Mn^{2+}$ accumulates in the cardiomyocytes in a more additive fashion, bound to intracellular proteins.

Allowing direct assessment of myocardial calcium influx, the $Mn^{2+}$ ion is useful not only as an imaging contrast agent, but also as a physiological and/or metabolic tracer.

Manganese enters the cardiomyocytes, i.e. cardiac muscle cells, in proportion to calcium uptake through L-type voltage-gated calcium channels located in the T-tubule membrane. Manganese accumulated in cardiomyocytes leads to a concentration dependent increase in the longitudinal relaxation rate R1 in normal myocardium (Eq. 2), which causes said reduction of T1.

$$\Delta R1_{Mn} = r_{1Mn} * \Delta C_{Mn} \quad \text{(Eq. 2)}$$

$\Delta C_{Mn}$ is the change in manganese concentration, and $r_{1Mn}$ is the relaxivity of manganese. The notation A is used to show a change from a baseline value. In Eq. 2, this baseline value is the value before the injection of a contrast agent, i.e. at time t=0. The change in longitudinal relaxation rate ($\Delta R1_{Mn}$) is closely proportional to the cell manganese concentration over a very large range. Hence, a T1 mapping MRI technique can be used to measure the concentration of manganese in tissue such as the myocardium and in fluids such as plasma and extracellular fluid (ECF) from Eq. 3.

$$\Delta C_{Mn} = \frac{\Delta\left(\frac{1}{T1}\right)}{r_{1Mn}} \quad \text{(Eq. 3)}$$

In certain instances, the manganese in the extracellular fluid is in equilibrium with plasma, so the manganese concentration in the ECF may be substituted with the manganese concentration in plasma (Eq. 4a).

$$C_{ECF}(t) = C_{Plasma}(t) \quad \text{(Eq. 4a)}$$

However, in other instances there is not equilibrium between plasma and ECF, and the manganese concentration in the ECF is equal to the plasma concentration multiplied with a constant, $K_{ECF}$ (Eq. 4b).

$$C_{ECF} = K_{ECF} * C_{Plasma} \quad \text{(Eq. 4b)}$$

The manganese uptake in cardiomyocytes is irreversible within the time frames used in a clinical MRI examination. The manganese uptake is proportional to the concentration in the ECF, and the ECF concentration may be in steady state with plasma. Hence the rate of uptake and rate of increase in intracellular manganese concentration at a certain time point t, $dC_{cell}(t)/dt$, is proportional to the plasma concentration (Eq. 5).

$$K_{cell}^{Mn}$$

represents the cardiomyocyte cellular manganese uptake rate.

$$dC_{cell}(t)/dt = K_{cell}^{Mn} * K_{ECF} * C_{Plasma}(t) \quad \text{(Eq. 5)}$$

The cardiomyocytes represent a tissue compartment with irreversible uptake of manganese, which enables kinetic modelling of irreversible uptake of manganese as a tracer.

If the plasma concentration of the contrast agent is constant, $P(t)=P_0$, the change in the 1/T1 relaxation rate from a region of interest (ROI) positioned over the myocardium will have a constant part from the reversible extracellular volume fraction (ECV), i.e. the volume of a tissue, which is not occupied by cells, and a linearly increasing part from the irreversible compartment as function of time (Eq.

6). A region of interest comprises at least one voxel (3D pixel), generated by standard MRI software.

$$ROI(t)=ECV*K_{ECF}*P_0+K_{ROI}*P_0*t \quad \text{(Eq. 6)}$$

ROI(t) is the change in relaxation rate caused by manganese in the region of interest at time t, measured by the MRI instrument for at least one, commonly several, voxels. Division by $P_0$ gives Eq. 7.

$$\frac{ROI(t)}{P_0}=ECV*K_{ECF}+K_{ROI}*t \quad \text{(Eq. 7)}$$

It follows from Eq. 7 that the plot of ROI(t)/$P_0$ is a straight line with time as the X axis, the Y-intercept being equal to the extracellular volume fraction (ECV) if $K_{ECF}$=1 and the slope $K_{ROI}$ equal to the irreversible uptake rate of the contrast agent, which is the inverse of the time it will take to raise the ROI signal by the amount in plasma.

However, in practical situations, the concentration of contrast agent in plasma is not constant and the change in relaxation rate caused by manganese in the region of interest follows the differential equation Eq. 8.

$$\frac{dROI(t)}{dt}=K_{ROI}*P(t) \quad \text{(Eq. 8)}$$

Patlak and coworkers [Patlak, C. S.; Blasberg R G, Fenstermacher J D (Graphical evaluation of Blood-to-Brain Transfer Constants from Multiple-Time Uptake Data) *Journal of Cerebral Blood Flow and Metabolism* 1983, 3:1-7] derived a method to normalise time to give a straight line also in the case of variations in the plasma concentration (Eq. 9).

$$\frac{ROI(t)}{P(t)}=V_r+K_{ROI}\frac{\int_0^t P(t)dt}{P(t)} \quad \text{(Eq. 9)}$$

Here, the plasma concentration needs to be integrated over time and, for each time point, the x value (normalised time) is calculated as the integral at each time point divided by the corresponding plasma concentration. $V_r$ is related to the volume fraction of the reversible compartment in the model, which in the myocardium corresponds to the ECV.

Skjold et al. [Skjold A, Kristoffersen A, Vangberg T R, Haraldseth O, Jynge P, Larsson H B W (An Apparent Unidirectional Influx Constant for Manganese as a Measure of Myocardial Calcium Channel Activity) *Journal Of Magnetic Resonance Imaging* 2006, 24:1047-1055] adapted this Patlak plot method for use in MRI to estimate the unidirectional transfer constant $K_i$ for uptake of manganese in cardiac tissue.

Whereas Skjold found that the estimates of the transfer constant $K_i$ using the slope of the Patlak plot was not significantly different from that obtained with the use of other, much more complex analyses involving solving several partial differential equations, the estimates for the reversible component using the intercept were "in most cases negative". A negative value for the extracellular volume fraction is physiologically impossible in itself and also implies that the value of the intercept cannot be used in other calculations of uptake parameters. Thus, although useful to differentiate viable tissue from nonviable tissue, the model as proposed by Skjold may lead to incorrect and paradoxically wrong estimates of the cellular flux rates and other tissue properties. The reason for these non-physiological values for the intercept is that it is a mathematical term collecting the bias in the regression when the errors are minimised, rather than an estimate of a physiologic parameter in itself.

Spath et al. [Spath, N. B; Singh, T.; Papanastasiou, G.; Kershaw, L; Baker, A. H; Janiczek, R. L; Gulsin, G. S; Dweck, M. R.; McCann, G.; Newby, D. E.; Semple, S. I. (Manganese-enhanced magnetic resonance imaging in dilated cardiomyopathy and hypertrophic cardiomyopathy) *European Heart Journal—Cardiovascular Imaging* 2020, doi:10.1093/ehjci/jeaa273 also applied the Patlak plot method to analyse MRI data from patients with dilated and hypertrophic cardiomyopathies with and without fibrosis. In patients with fibrosis, the intercept of the Patlak plot was found to be >1, implying an estimated fractional ECV>100%, which is physiologically impossible and rules out the use of the intercept for any meaningful estimate of the ECV and to improve the estimates of the cellular uptake rate constant.

WO2008087445 proposes a method to detect cardiac remodelling by identifying tissue with a continuing reduction in T1 after contrast injection as viable, whereas tissue with a transient reduction in T1 is defined as non-viable. No attempts to quantify the rate of uptake in cardiomyocytes is proposed in WO2008087445.

Presently used methods for estimating the cardiomyocyte manganese uptake rate and ECV are associated with certain problems. Firstly, the rate constant of manganese uptake determined by the slope of the Patlak plot is a measure of the uptake of manganese in a unit of tissue and not of the uptake in the cardiomyocyte volume fraction of the tissue. Hence, state of the art technologies do not differentiate between the quantity of cardiomyocytes versus the manganese uptake rate of the cardiomyocytes, potentially leading to false conclusions about the cellular calcium handling. Secondly, the currently used methods for kinetic modelling fail to determine the y intercept of the Patlak plot as a physiological measurement of the extracellular volume fraction, further showing the inadequateness of this method for estimating cardiomyocyte manganese uptake rate and thus cardiomyocyte calcium handling.

A correct determination of the cardiomyocyte manganese uptake rate is important in order to correctly evaluate cellular calcium handling, and thus particularly useful in the diagnosis and treatment of patients suffering from heart failure, particularly heart failure with preserved ejection fraction (HFpEF).

Hence, there is a need for improved methods for determining cardiomyocyte calcium handling.

BRIEF SUMMARY OF THE INVENTION

In a first aspect, the present invention relates to a method for determining a cardiomyocyte cellular manganese uptake rate of a subject as defined in claim 1. The method comprises the steps of:

i) performing, at a time point $t_i$=0, a first longitudinal relaxation time measurement $T1_{blood}(0)$ of the blood of the subject, and performing, for a section of the heart of the subject, a first longitudinal relaxation time measurement $T1_{myocardium}(0)$ of the myocardium of the subject;

ii) administering to the subject a dose $d_a$ of a contrast agent at a dosing rate of $D_a$ μmol/kg/min, wherein the contrast agent comprises a manganese contrast agent having a stability constant of 10-18, or a pharmaceutically acceptable salt thereof, and wherein the administration is completed at a time $t_a$;

iii) performing, at one or more time points $t_i$ during the administration in step ii), 0-5 minutes before $t_a$, measurements $T1_{blood}(t_i)$ of the longitudinal relaxation time of the blood of the subject, and performing, for said section of the heart of the subject, at the same time points $t_i$, measurements $T1_{myocardium}(t_i)$ of the longitudinal relaxation time of the myocardium of the subject;

iv) performing, at one or more time points $t_i$ 0-60 minutes after $t_a$, measurements $T1_{blood}(t_i)$ of the longitudinal relaxation time of the blood of the subject and, for said section of the heart of the subject, at the same time points $t_i$, measurements $T1_{myocardium}(t_i)$ of the longitudinal relaxation time of the myocardium of the subject;

v) calculating the change in myocardial relaxation rate $\Delta R1_{myocard}(t_i)$ for each of the time points $t_i$ of steps i), iii) and iv) according to the formula $$\Delta R1_{myocard}(t_i) = \frac{1}{T1_{myocard}(t_i)} - \frac{1}{T1_{myocard}(0)};$$

vi) obtaining a haematocrit value hct for the subject;

vii) calculating the change in plasma relaxation rate $\Delta R1_{plasma}(t_i)$ for each of the time points $t_i$ of steps i), iii) and iv) according to the formula $$\Delta R_{plasma}(t_i) = \frac{\frac{1}{T1_{blood}(t_i)} - \frac{1}{T1_{blood}(0)}}{1 - hct};$$

viii) estimating the integrals $$\int_0^{t_i} \Delta R1_{plasma}(t)dt$$

using each of the $\Delta R1_{plasma}(t_i)$ values of step vii);

ix) obtaining an estimate of the ECV for said section of the heart of the subject;

x) defining an equation for a straight line y=A+Bx, wherein $$y = \frac{\Delta R1 myocardium(t)}{\Delta R1 plasma(t)},$$

$$A = K_{ECF} * ECV,$$

wherein $K_{ECF}$ is a constant, $$B = K_{cell}^{\Delta R1} * K_{ECF}$$

and $$x = \frac{(1 - ECV) * \int_0^t \Delta R1 plasma(t)dt}{\Delta R1 plasma(t)};$$

xi) estimating the slope B, and thus the appearent cardiomyocyte cellular manganese uptake rate $$K_{cell}^{Mn} * K_{ECF} = B,$$

by a linear regression method with forced intercept $A=K_{ECF}$*ECV.

In a second aspect, the present invention relates to a contrast agent comprising a manganese contrast agent, or a pharmaceutically acceptable salt thereof, for use in a method for in vivo diagnosis of heart failure or heart disease in a subject, wherein the contrast agent has a stability constant of 10-18, and wherein the method comprises the steps of the method defined above, and further comprises the step of xii) comparing the $$K_{cell}^{Mn}$$

value to one or more reference values for the relaxivity change in order to diagnose a heart disease in the subject.

In a third aspect, the present invention relates to a computer-implemented method of determining a cardiomyocyte cellular manganese uptake rate in a subject as defined herein, the method comprising i) receiving from the picture archiving and communication PACS system of an MRI instrument scan data from a first longitudinal relaxation time measurement $T1_{blood}(0)$ of blood of the subject and data from a first longitudinal relaxation time measurement $T1_{myocardium}(0)$ of the myocardium of the subject, performed for a section of the heart of the subject;

ii) receiving from the PACS system of an MRI instrument series of scan data from one or more measurements $T1_{blood}(t_i)$ of the longitudinal relaxation time of the blood of the subject and one or more measurements $T1_{myocardium}(t_i)$ of the longitudinal relaxation time of the myocardium of the subject, performed for said section of the heart of the subject, wherein the $T1_{blood}(t_i)$ measurements and the $T1_{myocardium}(t_i)$ measurements have been performed at one or more time points $t_i$ during administration to the subject of a dose $d_a$ of a contrast agent at a dosing rate of $D_a$ μmol/kg/min, the contrast agent comprising a manganese contrast agent having a stability constant of 10-18, or a pharmaceutically acceptable salt thereof, the administration being completed at a time $t_a$, iii) receiving from the PACS system of an MRI instrument pulse sequence series data from one or more measurements $T1_{blood}(t_i)$ of the longitudinal relaxation time of the blood of the subject and from one or more measurements $T1_{myocardium}(t_i)$ of the longitudinal relaxation time of the myocardium of the subject, performed for said section of the heart of the subject, wherein the measurements have been performed at one or more time points $t_i$ up to 60 minutes after $t_a$;

iv) calculating the change in myocardial relaxation rate $\Delta R1_{myocard}(t_i)$ for each of the time points $t_i$ of steps i), ii) and iii) according to the formula $$\Delta R1_{myocard}(t_i) = \frac{1}{T1_{myocard}(t_i)} - \frac{1}{T1_{myocard}(0)};$$

v) receiving a haematocrit value, hct, for the subject;

vi) calculating the change in plasma relaxation rate $\Delta R1_{plasma}(t_i)$ for each of the time points $t_i$ of steps i), ii) and iii) according to the formula $$\Delta R1_{plasma}(t_i) = \frac{\frac{1}{T1_{blood}(t_i)} - \frac{1}{T1_{blood}(0)}}{1 - hct};$$

vii) estimating the integrals $$\int_0^{t_i} \Delta R1_{plasma}(t)dt$$

using each $\Delta R1_{plasma}(t_i)$ value of step vi);

viii) receiving an estimate of the ECV for said section of the heart of the subject;

ix) defining an equation for a straight line y=A+Bx, wherein $$y = \frac{\Delta R1 myocardium(t)}{\Delta R1 plasma(t)},$$

$A=K_{ECF}$*ECV, wherein $K_{ECF}$ is a constant, $$B = K_{cell}^{\Delta R1} * K_{ECF}$$

and $$x = \frac{(1 - ECV) * \int_0^t \Delta R1 plasma(t)dt}{\Delta R1 plasma(t)};$$

x) estimating the slope B, and thus the apparent cardiomyocyte cellular manganese uptake rate $$K_{cell}^{Mn} * K_{ECF} = B,$$

by a linear regression method with forced intercept $A=K_{ECF}$*ECV.

In a fourth aspect, the present invention relates to a data processing apparatus comprising means for carrying out said computer-implemented method, as defined herein.

In a fifth aspect, the present invention relates to a computer program as defined herein, the computer program comprising instructions which, when the program is executed by a computer, cause the computer to carry out said computer-implemented method.

In a sixth aspect, the present invention relates to a computer-readable medium as defined herein, the computer-readable medium having stored thereon said computer program.

DETAILED DESCRIPTION OF THE INVENTION

Figure 1:
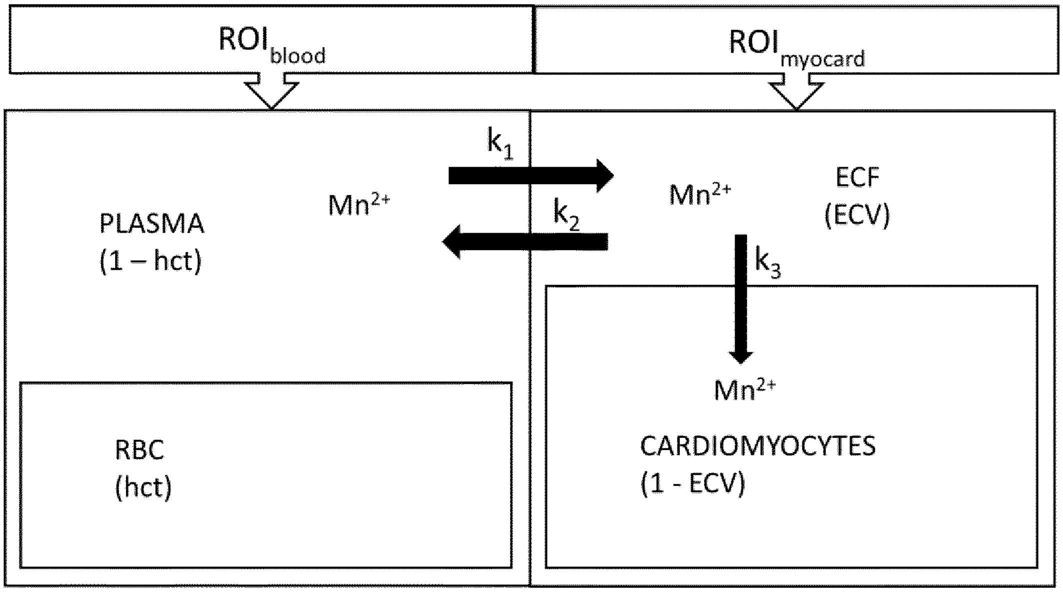
FIG. 1 illustrates the tissue compartments used for T1 measurements in regions of interest (ROIs) in blood and myocardium and for measurements of $Mn^{2+}$ fluxes, $k_1$, $k_2$ and $k_3$

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The uptake rate constant provided by the method proposed by Patlak and Skjold is a measure of the rate of irreversible uptake in a region of interest in the myocardium. Since the spatial resolution of MRI does not allow direct imaging at a cellular level, a region of interest will consist of a mixture of extracellular fluid and cells. Therefore, the method proposed in the prior art does not distinguish between a reduction in the cellular flux rate and a reduction in the number of cells. This has important clinical implication since a therapy directed towards the cellular calcium channel activity has no effect where the cells have been lost due to e.g. fibrosis.

The invention provides a novel method to measure the cellular flux rate and can therefore distinguish between variations in calcium metabolism at a cellular level and variations caused by changes in the cellular partial volume.

In the myocardium, the tissue consists of ECF and cells, therefore, the uptake rate at a tissue level can be transformed to an estimate for the cellular flux by the equation $$k_{cell} = k_{ROI}/((1-ECV)*K_{ECF}) \quad \text{(Eq. 10)}$$

Rearranging Eq. 9 gives the function for the relaxivity of a region of interest in the myocardium:

$$\Delta R1_{ROI}(t) = ECV*K_{ECF}*\Delta R1_{plasma}(t) + K_{cell}*K_{ECF}*(1-ECV)*\int_0^t \Delta R1\,plasma(t)dt \quad \text{(Eq. 11)}$$

From Eq. 11, it can be seen that information about the ECV can best be obtained from variations in the plasma relaxivity, whereas information about the irreversible compartment can best be obtained if the plasma concentration is stable and the integration robust to variations. The methods recommended in the prior art have prioritized measurements of $k_{ROI}$ with stable or slowly changing plasma values, which has led to poor signal to noise for measurement of changes in plasma relaxivity and ECF estimation. Therefore, the methods proposed in the prior art have failed to provide an estimate of the relaxation rate in the ECF. Skjold's method of slow infusion and measuring over long time intervals in most cases led to a negative value for the ECV, which is physiologically impossible and meaningless to apply for estimation of $k_{cell}$ according to Eq. 10.

The present invention provides methods for estimating calcium uptake at a cellular level. The methods and uses of the invention employ imaging in order to measure the cellular manganese uptake rate and determines the manganese uptake rate at the cellular level as opposed to only at a tissue level, and provides a novel transfer constant for cellular manganese uptake rate, $$K_{cell}^{Mn}.$$

The methods and uses of the invention are based on cellular uptake of metal ions via L-type calcium channels, measuring the inward flux of the metal ions through the L-type calcium channels using a medical imaging method. Preferably, the medical imaging method is MRI. Preferably, the metal ions are $Mn^{2+}$ ions. Hence, MEMRI is advantageously used in the methods and uses of the invention.

The methods and uses of the invention may be useful for various tissues and organs that comprise cells having L-type calcium channels. In particular, the methods and uses of the invention are useful for the heart, in particular the myocardium.

In one aspect, the invention provides a method for determining a cellular manganese uptake rate of a subject using MRI. The method allows for a direct estimate of calcium uptake at a cellular level.

In one embodiment, the invention provides a method for determining a cardiomyocyte cellular manganese uptake rate $$K_{cell}^{Mn}$$

of a subject, the method comprising the steps of:

i) performing, at a time point $t_i$=0, a first longitudinal relaxation time measurement $T1_{blood}(0)$ of the blood of the subject, and performing, for a section of the heart of the subject, a first longitudinal relaxation time measurement $T1_{myocardium}(0)$ of the myocardium of the subject;

ii) administering to the subject a dose $d_a$ of a contrast agent at a dosing rate of $D_a$ μmol/kg/min, wherein the contrast agent comprises a manganese contrast agent having a stability constant of 10-18, or a pharmaceutically acceptable salt thereof, and wherein the administration is completed at a time $t_a$;

iii) performing, at one or more time points $t_i$ during the administration in step ii), 0-5 minutes before $t_a$, measurements $T1_{blood}(t_i)$ of the longitudinal relaxation time of the blood of the subject, and performing, for said section of the heart of the subject, at the same time points $t_i$, measurements $T1_{myocardium}(t_i)$ of the longitudinal relaxation time of the myocardium of the subject;

iv) performing, at one or more time points $t_i$ 0-60 minutes after $t_a$, measurements $T1_{blood}(t_i)$ of the longitudinal relaxation time of the blood of the subject and, for said section of the heart of the subject, at the same time points $t_i$, measurements $T1_{myocardium}(t_i)$ of the longitudinal relaxation time of the myocardium of the subject;

v) calculating the change in myocardial relaxation rate $\Delta R1_{myocard}(t_i)$ for each of the time points $t_i$ of steps i), iii) and iv) according to the formula $$\Delta R1_{myocard}(t_i) = \frac{1}{T1_{myocard}(t_i)} - \frac{1}{T1_{myocard}(0)}; \quad \text{(Eq. 12)}$$

vi) obtaining a haematocrit value hct for the subject;

vii) calculating the change in plasma relaxation rate $\Delta R1_{plasma}(t_i)$ for each of the time points $t_i$ of steps i), iii) and iv) according to the formula $$\Delta R1_{plasma}(t_i) = \frac{\frac{1}{T1_{blood}(t_i)} - \frac{1}{T1_{blood}(0)}}{1-hct}; \quad \text{(Eq. 13)}$$

viii) estimating the integrals $$\int_0^{t_i} \Delta R1_{plasma}(t)dt$$

using each of the $\Delta R1_{plasma}(t_i)$ values of step vii);

ix) obtaining an estimate of the ECV for said section of the heart of the subject;

x) defining an equation for a straight line y=A+Bx, wherein $$y = \frac{\Delta R1 myocardium(t)}{\Delta R1 plasma(t)},$$

$A=K_{ECF}$*ECV, wherein $K_{ECF}$ is a constant, $$B = K_{cell}^{\Delta R1} * K_{ECF}$$

and $$x = \frac{(1 - ECV) * \int_0^t \Delta R1 plasma(t)dt}{\Delta R1 plasma(t)};$$

xi) estimating the slope B, and thus the appearent cardiomyocyte cellular manganese uptake rate $$K_{cell}^{Mn} * K_{ECF} = B,$$

by a linear regression method with forced intercept $A=K_{ECF}$*ECV.

As used herein, "subject" means any human or non-human animal, and encompasses, and may be limited to, "patient".

According to the invention, the subject may be a human or a non-human animal, such as a human or non-human mammal. Preferably the subject is a human patient. The subject may be male or female. In some embodiments of the invention, the subject is an adult (i.e. 18 years of age or older). In certain embodiments, the subject is geriatric. In certain embodiments, the subject is not geriatric.

In step i), a first longitudinal relaxation time measurement $T1_{blood}(0)$ of blood of the subject and a first longitudinal relaxation time measurement $T1_{myocardium}(0)$ of the myocardium of the subject is performed for a section, of the heart of the subject. The measurements are performed at a time point $t_i$=0. This time point is before any administration of contrast agent to the subject. The section may be a short axis mid-ventricular cross-section. The $T1_{blood}(O)$ measurement may be performed for this section of the heart. Alternatively, the $T1_{blood}(O)$ measurement may be performed outside the MRI scanner, such as using a blood sample.

This "baseline" dataset of T1(0) data is for use as a reference for the changes in relaxivity that is measured in the following steps, according to Eq. 1, cf. Eq. 14 and Eq. 15.

$$\text{Baseline relaxivity in blood} = R1_{blood}(0) = \frac{1}{T1_{blood}(0)} \quad \text{(Eq. 14)}$$

$$\text{Baseline relaxivity in myocardium} = R1_{myocard}(0) = \frac{1}{T1_{myocard}(0)} \quad \text{(Eq. 15)}$$

The MRI employed in all relevant steps of the present invention may be carried out using conventional MRI equipment.

In step ii), a dose $d_a$ of a contrast agent is administered to the subject. As used herein, the terms "administer", "administration", and "administering" refer to providing, giving, and/or dosing by either a health practitioner or their authorised agent or under their direction, a formulation, preparation or composition according to the present disclosure. The contrast agent comprises a manganese contrast agent or a pharmaceutically acceptable salt thereof.

The uptake of manganese in the cardiomyocytes is dependent on release of manganese from the chelate in large enough quantities to be measurable within a 60 minutes' time frame, but small enough not to block the L-type channels and cause cardiotoxic effects. It is also preferred that the stability constant is lower, preferably 2-3 orders of magnitude lower, than that for zinc. This may allow transmetallation with zinc to occur, leading to slow release of manganese from the chelate. Thus, the contrast agent has a stability constant of 10-18, preferably 11-17, more preferably 14-16, most preferably 15.1. As used herein, the term "stability constant" refers to the equilibrium constant for the formation of a complex, e.g. a chelate, in solution. It can be seen as a measure of the strength of the interaction between the reagents that come together to form the complex.

In the methods and uses of the invention, a clinically acceptable amount of manganese is used. Conveniently, the dose $d_a$ may be 1-10 μmol/kg body weight, preferably 3-7 μmol/kg body weight, such as 5 μmol/kg body weight. The contrast agent is administered to the subject by infusion into the systemic vasculature at a dosing rate of $D_a$ μmol/kg/min. The dosing rate $D_a$ may be in the range 0.3-8 μmol/kg/min, preferably 2-6 μmol/kg/min, more preferably 5 μmol/kg/min. These rates are readily achievable using conventional delivery equipment, such as an MRI compatible infusion pump. The infusion may be a bolus injection.

The administration typically lasts for 1-2 minutes, such as for about 1 minute. The time of completion of the administration is referred to as $t_a$.

In step iii), one or more measurements $T1_{blood}(t_i)$ of the longitudinal relaxation time of the blood of the subject are performed, and one or more measurements $T1_{myocardium}(t_i)$ of the longitudinal relaxation time of the myocardium of the subject are performed for said section of the heart of the subject. The one or more $T1_{blood}(t_i)$ measurements and the one or more $T1_{myocardium}(t_i)$ are all performed during step ii), i.e. during administration of the contrast agent.

The measurements are performed at different points in time, collectively referred to as $t_i$. The $T1_{blood}(t_i)$ measurements should be performed at the same time points $t_i$ as the $T1_{myocardium}(t_i)$ measurements.

If only one of each measurement is performed, these measurements should be performed relatively close to the end of the administration, at $t_a$ (the time when the administration is completed). This timing ensures the presence of a large amount of contrast agent in the extracellular fluid of the myocardium. In some embodiments, the measurements are performed 0-2.5 minutes before $t_a$. Optionally, additional measurements may be performed at different time points $t_i$ 0-5 minutes before $t_a$, such as 0-2.5 minutes before $t_a$. For example, measurements may be performed as often as once every half minute. Such additional measurements will give data for a reliable estimate of the integral of the changes in plasma relaxation rate. The exact timing of these additional measurements is not essential, but they may advantageously be spread out in time. and they may be the same for all time points or they may differ.

In step iv), one or more measurements $T1_{blood}(t_i)$ of the longitudinal relaxation time of the blood of the subject are performed, and one or more measurements $T1_{myocardium}(t_i)$ of the longitudinal relaxation time of the myocardium of the subject are performed for said section of the heart of the subject. The one or more $T1_{blood}(t_i)$ measurements and the one or more $T1_{myocardium}(t_i)$ are all performed after step iii), i.e. after completion of the administration of the contrast agent. The measurements are performed at different points in time, collectively referred to as $t_i$, between 0 and 60 minutes after $t_a$. The $T1_{blood}(t_i)$ measurements should be performed at the same time points $t_i$ as the $T1_{myocardium}(t_i)$ measurements.

At least one $T1_{blood}(t_i)$ measurement and one $T1_{myocardium}(t_i)$ measurement must be performed. Advantageously, an additional 5-10 measurements are performed, giving the advantage of providing data for a reliable estimate of the integral of the changes in plasma relaxation rate. Time intervals between two time points $t_i$ may be 0.5-7 minutes, preferably 1-5 minutes, such as 1-3 minutes, more preferably 2.5 minutes, and they may be the same for all two time points or they may differ.

In step v), the change in relaxation rate for the myocardium, $\Delta R1_{myocard}(t_i)$, relative to the myocardial relaxation rate $R1_{myocard}(0)$ before administration of the contrast agent to the subject, is calculated for each of the time points $t_i$ of steps i), iii) and iv). Eq. 12, which follows from Eq. 15, is used, wherein $T1_{myocard}(0)$ is the value measured in step ii).

$$\Delta R1_{myocard}(t_i) = \frac{1}{T1_{myocard}(t_i)} - \frac{1}{T1_{myocard}(0)} \quad \text{(Eq. 12)}$$

Hence for each of the one or more time points $t_i$ of step iii) and for each of the one or more time points $t_i$ of step iv), a corresponding change in relaxation rate for the myocardium relative to the "baseline" value is calculated, which is $\Delta R1_{myocard}(t_i)$ In step vi), the haematocrit value (hct) for the subject, i.e. the volume fraction of red blood cells in the blood of the subject, is obtained. The haematocrit is given as a dimensionless number between 0 and 1. The haematocrit is useful for the estimation of plasma values since the manganese contrast agent is not present in red blood cells. The hct value may be obtained from a previous measurement or estimate, advantageously performed up to 4 weeks prior to the MRI method steps of the invention. The hct value may be obtained by measurement. Several methods for this measurement are known to the skilled person, including microhematocrit centrifugation, and optical methods such as spectrophotometry. Preferably, the haematocrit measurement is performed by microhematocrit centrifugation. Step vi) may be performed at any time before or after any of steps i)-v).

In step vii), the change in relaxation rate for the blood plasma, $\Delta R1_{plasma}(t_i)$, relative to the plasma relaxation rate $R1_{plasma}(0)$ before administration of the contrast agent to the subject, is calculated for each of the time points $t_i$ of steps i), iii) and iv). Eq. 13, which follows from Eq. 14, is used, wherein $T1_{plasma}(0)$ is the value measured in step ii) and hct is the haematocrit value obtained in step i).

$$\Delta R1_{plasma}(t_i) = \frac{\frac{1}{T1_{blood}(t_i)} - \frac{1}{T1_{blood}(0)}}{1 - hct} \quad \text{(Eq. 13)}$$

Since the haematocrit is the volume fraction of red blood cells in blood, and the plasma is the liquid part of the blood, the division by (1−hct) allows the use of measurements performed on blood to determine the $\Delta R1_{plasma}(t_i)$ value for plasma. For each of the one or more time points $t_i$ of step iii) and for each of the one or more time points $t_i$ of step iv), a corresponding change in relaxation rate for the plasma relative to the "baseline" value is calculated, which is $\Delta R1_{plasma}(t_i)$.

In step viii), the $\Delta R1_{plasma}(t_i)$ values calculated in step vii) allow the estimation of the integral from time zero to the n'th measurement time $$\int_0^{t_n} \Delta R1_{plasma}(t)dt.$$

The integral may be e.g. estimated by applying the trapezoidal method, as shown in Eq. 16, $$\int_{t_{n-1}}^{t_n} \Delta R1_{plasma}(t)dt \approx (t_n - t_{n-1})\frac{\Delta R1_{plasma}(t_n) + \Delta R1_{plasma}(t_{n-1})}{2} \quad \text{(Eq. 16)}$$

Other methods to estimate the integral can be the Simpson's rule for equally spaced time intervals $t_n$ $$\int_{t_{n-2}}^{t_n} \Delta R1_{plasma}(t)dt \approx \frac{(t_n - t_{n-2})}{6} * (\Delta R1_{plasma}(t_{n-2}) + 4 * \Delta R1_{plasma}(t_{n-1}) + \Delta R1_{plasma}(t_n)) \quad \text{(Eq. 17)}$$

Such methods are well-known to the person skilled in the art.

In step ix), a value for the ECV in said section of the heart is obtained. The ECV value may, for example, be obtained by measuring pre- and 20 minutes post-contrast myocardial T1 after injection of a gadolinium contrast agent corrected for blood-pool T1 and serum haematocrit, performed 1-30 days before or 1-30 days after steps i)-iv). The ECV may then be calculated according to eq. 18.

$$ECV = \frac{\Delta(1/T1_{Myocardium})}{\Delta(1/T1_{Bloodpool})}[1 - hct] \quad \text{(Eq. 18)}$$

The ECV value may alternatively be obtained by any method known to the skilled person. Step ix) may be performed at any time before or after any of steps i)-viii). The obtained ECV value is used in the subsequent steps.

In step x), an estimate of the rate constant for cardiomyocyte intracellular relaxivity increase $$K_{cell}^{\Delta R1},$$

and thus the cardiomyocyte cellular manganese uptake rate $$K_{cell}^{Mn},$$

is calculated from the relationship derived from Eq. 10 and Eq. 11 (Eq. 19).

$$\Delta R1_{myocardium}(t) = ECV * K_{ECF} * \Delta R1_{plasma}(t) + K_{cell}^{\Delta R1} * K_{ECF} * (1-ECV) * \int_0^t \Delta R1 plasma(t)dt \quad \text{(Eq. 19)}$$

Division by $\Delta R1_{plasma}(t)$ gives Eq. 20.

$$\frac{\Delta R1 myocardium(t)}{\Delta R1 plasma(t)} = ECV * K_{ECF} + K_{cell}^{\Delta R1} * K_{ECF} \frac{(1-ECV) * \int_0^t \Delta R1 plasma(t)dt}{\Delta R1 plasma(t)} \quad \text{(Eq. 20)}$$

As provided in the introduction, when the manganese in equilibrium with plasma, the concentration in the ECF equals the concentration in the plasma (Eq. 4a). This is the case when a gadolinium contrast agent is used. However, under other conditions, a more precise indication of the ECF concentration is provided by Eq. 4b, and the plasma concentration should be multiplied with a constant $K_{ECF}$.

$$C_{ECF}(t) = K_{ECF} * C_{Plasma}(t) \quad \text{(Eq. 4b)}$$

Reference is made to FIG. 1, showing that the constant $K_{ECF}$ is provided by Eq. 21.

$$K_{ECF} = \frac{K1}{K2 + K3} \quad \text{(Eq. 21)}$$

K1 is the rate constant for diffusion from plasma into the ECF, k2 is the rate constant for diffusion from the ECF back to plasma and k3 is the rate constant for transport from the ECF into the cell compartment. Example 3, referring to a study wherein data from 5 patients with hypertrophic cardiomyopathia have been analyzed, further provides data supporting the identification of $K_{ECF}$. In one embodiment, $K_{ECF}$ is a constant of 0.6 to 1.0. When using gadolinium, the concentration in the plasma equals the concentration in the ECF and $K_{ECF}$=1. In one embodiment $K_{ECF}$=0.72, as shown in Example 3. Hence, in a preferred embodiment, the intercept of the line described in Eq. 20 is 0.72*ECV.

The sought apparent cardiomyocyte cellular manganese uptake rate, $$K_{cell}^{Mn} * K_{ECF},$$

is the slope of the line, $$K_{cell}^{\Delta R1} * K_{ECF}$$

In step xi), $$K_{cell}^{\Delta R1} * K_{ECF}$$

is calculated. The slope can be calculated with linear regression techniques with a forced y intercept equal to $K_{ECF}$*ECV, such as by relative linear regression (Eq 22):

$$K_{cell}^{Mn} * K_{ECF} = K_{cell}^{\Delta R1} * K_{ECF} = \frac{\overline{y} - K_{ECF} * ECV}{\overline{x}}. \quad \text{(Eq. 22)}$$

Alternatively, other methods of linear regression, known to the skilled person, may be applied, such as absolute linear regression (Eq. 23).

$$K_{cell}^{Mn} * K_{ECF} = \frac{\sum_1^N x_i(y_i - K_{ECF} * ECV)}{\sum_1^N x_i x_i} \quad \text{(Eq. 23)}$$

In yet another alternative, $$K_{cell}^{\Delta R1}$$

can be calculated by solving Eq. 19 by multiple linear regression where $\Delta R1_{myocardium}(t)$ is the dependent variable and $\Delta R1_{plasma}(t)$ and $$(1-ECV) * \int_0^t \Delta R1 \text{plasma}(t)dt$$

are the two independent variables.

Because the increase in the cardiomyocyte intracellular relaxivity is directly dependent on the amount of manganese present in the cardiomyocytes, the cardiomyocyte cellular manganese uptake rate $$K_{cell}^{Mn}$$

is equal to the rate constant for cardiomyocyte intracellular relaxation rate increase $$K_{cell}^{\Delta R1}.$$

Importantly, the uptake of manganese in cardiomyocytes is irreversible within the time frames used in the method. The fact that the uptake can be seen as irreversible, allows the use of $$K_{cell}^{Mn}$$

to estimate the manganese cellular uptake rate of the cardiomyocytes of the subject, and thus also to determine the subject's cardiomyocyte calcium handling.

FIG. 1 illustrates the four-compartment model used for kinetic analysis of cardiomyocyte manganese uptake, consisting of red blood cells (RBC), blood plasma (PLASMA), myocardial extracellular fluid (ECF) and myocardial intracellular space (CARDIOMYOCYTE). During MR imaging, T1 values are collected from regions of interest in blood ($ROI_{blood}$) and myocardium ($ROI_{myocard}$). The partial volume in the respective region of interest is shown in parentheses. Whereas the influx of manganese into the cardiomyocyte is irreversible, the ECF is in a dynamic, reversible steady state with plasma, allowing the plasma concentration to be used as input value for assessment of the irreversible uptake constant $$K_{cell}^{Mn}$$

into the cardiomyocytes. The figure shows that when the manganese concentration in the ECF is in dynamic equilibrium, $K_{ECF}$=K1/(K2+K3). With reference to Example 3, assuming that the rate constant for diffusion between plasma and the ECF is the same in both directions, K1=K2 and K3/K1=1/$K_{ECF}$−1=1/0.72−1=0.40. This analysis shows that the rate constant for irreversible uptake in this case is 40% of the rate constant for diffusion between plasma and the ECF. When the ratio between the manganese concentration in the ECF and plasma can be estimated, the apparent cellular rate constant $$K_{cell}^{Mn} * K_{ECF}$$

can be converted to the actual cellular uptake rate constant $$K_{cell}^{Mn}$$

by division with $K_{ECF}$.

The $$K_{cell}^{Mn}$$

value of the invention is more correct than corresponding values reported in prior art for several reasons:

The equation of step viii) is corrected for haematocrit to give a correct plasma relaxation rate, $\Delta R1_{plasma}(t_i)$.

The slope of the myocardial relaxation rate curve is correctly determined with the restrictions given by using a forced $K_{ECF}$*ECV y-intercept.

The slope of the myocardial relaxation rate curve is corrected for the fractional volume of the cells.

The final transfer constant, $$K_{cell}^{Mn},$$

for the irreversible cardiomyocyte uptake is corrected for the ratio between the manganese concentration in ECF and plasma=$K_{ECF}$.

The method is useful for determining the cardiomyocyte cellular manganese uptake rate of a subject. The method may be used for determining the manganese uptake rate and the calcium uptake rate of the subject, also without the aim of establishing a diagnosis, such as a part of an MRI study.

In another aspect, the invention relates to a contrast agent comprising a manganese contrast agent, or a pharmaceutically acceptable salt thereof, for use in a method for in vivo diagnosis of a heart condition in a subject, such as for diagnosis of heart disease, such as for diagnosis of heart failure in a subject using MRI.

In one embodiment, the invention relates to a contrast agent comprising a manganese contrast agent, or a pharmaceutically acceptable salt thereof, for use in a method for in vivo diagnosis of heart failure in a subject, wherein the contrast agent has a stability constant of 10-18, and wherein the method comprises steps i)-xi) presented above, and further comprises the step of xii) comparing the $$K_{cell}^{Mn}$$

value to one or more reference values for calcium metabolism in order to diagnose a heart disease in the subject. A reference value from a control individual or a control group, such as a healthy individual or a group of healthy individuals, may be used for such comparison.

In one embodiment, the invention relates to a contrast agent comprising a manganese contrast agent, or a pharmaceutically acceptable salt thereof, for use in a method for in vivo diagnosis of heart failure in a subject, wherein the contrast agent has a stability constant of 10-18, and wherein the method comprises the steps of i) performing, at a time point $t_i$=0, a first longitudinal relaxation time measurement $T1_{blood}(0)$ of the blood of the subject, and performing, for a section of the heart of the subject, a first longitudinal relaxation time measurement $T1_{myocardium}(0)$ of the myocardium of the subject;

ii) administering to the subject a dose $d_a$ of a contrast agent at a dosing rate of $D_a$ μmol/kg/min, wherein the contrast agent comprises a manganese contrast agent having a stability constant of 10-18, or a pharmaceutically acceptable salt thereof, and wherein the administration is completed at a time $t_a$;

iii) performing, at one or more time points $t_i$ during the administration in step ii), 0-5 minutes before $t_a$, measurements $T1_{blood}(t_i)$ of the longitudinal relaxation time of the blood of the subject, and performing, for said section of the heart of the subject, at the same time points $t_i$, measurements $T1_{myocardium}(t_i)$ of the longitudinal relaxation time of the myocardium of the subject;

iv) performing, at one or more time points $t_i$ 0-60 minutes after $t_a$, measurements $T1_{blood}(t_i)$ of the longitudinal relaxation time of the blood of the subject and, for said section of the heart of the subject, at the same time points $t_i$, measurements $T1_{myocardium}(t_i)$ of the longitudinal relaxation time of the myocardium of the subject;

v) calculating the change in myocardial relaxation rate $\Delta R1_{myocard}(t_i)$ for each of the time points $t_i$ of steps i), iii) and iv) according to the formula $$\Delta R1_{myocard}(t_i) = \frac{1}{T1_{myocard}(t_i)} - \frac{1}{T1_{myocard}(0)}; \quad \text{(Eq. 12)}$$

vi) obtaining a haematocrit value hct for the subject;

vii) calculating the change in plasma relaxation rate $\Delta R1_{plasma}(t_i)$ for each of the time points $t_i$ of steps i), iii) and iv) according to the formula $$\Delta R1plasma(t_i) = \frac{\frac{1}{T1_{blood}(t_i)} - \frac{1}{T1_{blood}(0)}}{1 - hct}; \quad \text{(Eq. 13)}$$

viii) estimating the integrals $$\int_0^{t_i} \Delta R1_{plasma}(t)dt$$

using each of the $\Delta R1_{plasma}(t_i)$ values of step vii);

ix) obtaining an estimate of the ECV for said section of the heart of the subject;

x) defining an equation for a straight line y=A+Bx, wherein $$y = \frac{\Delta R1myocardium(t)}{\Delta R1plasma(t)},$$

$A=K_{ECF}$*ECV, $$B = K_{cell}^{\Delta R1}$$

and $$x = \frac{(1 - ECV) * K_{ECF} * \int_0^t \Delta R1plasma(t)dt}{\Delta R1plasma(t)};$$

xi) estimating the slope B, and thus the cardiomyocyte cellular manganese uptake rate $$K_{cell}^{Mn} * K_{ECF} = B,$$

by a linear regression method with forced intercept $A=K_{ECF}$*ECV; and xii) comparing the $$K_{cell}^{Mn}$$

value to one or more reference values for calcium metabolism in order to diagnose a heart disease in the subject.

Each of the steps i)-xi) are the steps described above for the aspect of a method for determining a cellular manganese uptake rate of a subject using MRI, and the disclosure relating to each of the steps for that aspect and embodiments thereof applies equally to this aspect and embodiments thereof.

The uses and methods of the invention measure the cardiomyocyte manganese uptake rate and the extracellular volume fraction, and determines the manganese uptake rate at the cellular level as opposed to only at a tissue level. The method therefore allows a separation of variations caused by cellular activity from variations caused by cell numbers and/or partial volume effects. It is the uptake rate, and not the anatomical distribution of the uptake, that is determined, and—importantly—the calcium channel activity rather than the total myocardial manganese uptake.

The invention is particularly useful in patients with heart failure, and/or with cardiomyopathies leading to heart failure, and specifically very useful in patients with suspected heart failure with preserved ejection fraction (HFpEF), dilated cardiomyopathy, hypertrophic cardiomyopathy, diabetic cardiomyopathy, hypertensive cardiomyopathy, and/or "broken heart syndrome" i.e. tako-tsubo cardiomyopathy. Advantageously, the invention provides an improved evaluation for cardiomyocyte calcium handling, aiding the diagnosis and treatment of heart failure. Hence, the subject may have been diagnosed with or is suspected of having heart failure and/or a cardiomyopathy leading to heart failure. Preferably, the subject has been diagnosed with or is suspected of having heart failure with HFpEF, dilated cardiomyopathy, hypertrophic cardiomyopathy, diabetic cardiomyopathy, hypertensive cardiomyopathy, and/or "broken heart syndrome" i.e. tako-tsubo cardiomyopathy. Even more preferably, the subject has been diagnosed with or is suspected of having heart failure with HFpEF.

Specifically, the present invention is very useful in the diagnosis of patients suffering from HFpEF, a form of heart failure in which the ejection fraction—the percentage of the volume of blood ejected from the left ventricle with each heartbeat divided by the volume of blood when the left ventricle is maximally filled—is normal, defined as greater than 50%. Approximately half of heart failure patients have preserved ejection fraction. HFpEF is characterised by abnormal diastolic function: there is an increase in the stiffness of the left ventricle, which causes a decrease in left ventricular relaxation during diastole. In the early stages of HFpEF, the strain on the tissue may lead to a compensatory reaction in the cardiomyocytes leading to increased uptake rate, as seen also in the remote areas after acute myocardial infarction. Thus, the invention enables the identification of increased calcium flux as a cause of myocardial stiffness. Later in the development of HFpEF, fibrous tissue starts to form leading to increased ECV. The invention may still detect cardiomyocyte hypercontraction as a contributor to stiffness, whereas the conventional method may erroneously report this as a reduction. If myocyte replacement becomes more significant, the conventionally used method will grossly underestimate the cellular function.

Preferred uses include, but are not limited to, the diagnosis of HFpEF, and the assessment of the contribution from cardiomyocytes to the ventricular stiffness. Other preferred uses include the diagnosis of dilated cardiomyopathy, hypertrophic cardiomyopathy, diabetic cardiomyopathy, hypertensive cardiomyopathy, and/or "broken heart syndrome" i.e. tako-tsubo cardiomyopathy. The invention is further useful for treatment monitoring; with repeated examinations, the development of disease and/or the responses to therapy can be followed.

The uses and methods of the invention allows the determination of the manganese uptake rate specifically in the myocyte volume fraction of the tissue. Such a determination is highly important because the myocyte volume fraction may be different in different diseases, meaning that observed variations in the rate of manganese uptake in MRI diagnosis may be caused either by variations in the rate of uptake in individual cells, or by variations in partial cell volume. The present invention may be used to separate between these two situations, and thus between different illnesses and diseases.

This positive effect results from the fact that separate data sets are used to estimate the ECV and the kinetics of cellular manganese uptake.

This advantage of the invention is in contrast to, and a significant improvement over, presently used methods. To illustrate: If the plasma concentration of manganese is constant, the uptake rate of manganese will be constant, and it will typically take 20 minutes before the myocardium manganese level has increased by the same amount as plasma. The Patlak method uses only one dataset to estimate the kinetics of the manganese uptake, and does not take into consideration the fact that manganese uptake physically only takes place in cardiomyocytes and not in the entire myocardium tissue volume. If the cardiomyocytes represent, typically, 75% of the tissue volume, "filling" these cells will not take 20 minutes, but 15. For the last five minutes, the cardiomyocytes will be taking up the additional amount of manganese required for the total myocardium tissue volume to increase by the same amount as plasma. The manganese uptake rate of the cardiomyocytes is thus 1/(15 min), i.e. 6.67 mL/100 g/min—and not 1/(20 min), i.e. 5 mL/100 g/min, as would be the result from the Patlak method. The importance of this systematic error is obvious in an example where 50% of the cardiomyocytes are dead or dysfunctional while the remaining 50% function as normal. In this example, "filling" the myocardium takes 40 minutes, even though the functional cardiomyocytes are in fact filled in only 15 minutes. The conclusion using the Patlak method will then—erroneously—be that the calcium channel activity has been reduced by 50%. While the fact that 50% of the cardiomyocytes are dead or dysfunctional may be discovered, evaluating the function of the remaining cardiomyocytes, i.e. whether they function normally, compensatory (more than normal function) or reduced, is not possible. Separating these two factors is important both in diagnosis, and also for treatment directed specifically towards e.g. the ion channel or hypertrophy.

Figure 2:
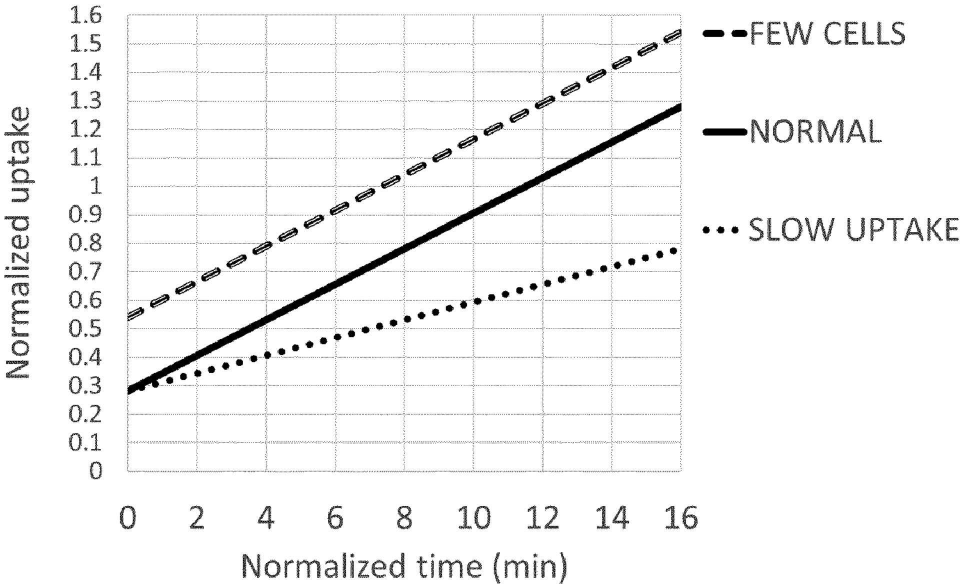
FIG. 2 shows a graphical representation of kinetic data analysis. The intercept represents the ECV, and the slope represents the value of the kinetic cellular uptake constant.

A graphical representation of kinetic data analysis is provided in FIG. 2, wherein the intercept represents the ECV, and the slope represents the value of the kinetic cellular uptake constant. With the invention, a change in L-type calcium channel flux rate leads to a changed slope, whereas a change in the partial cell volume leads to a change in the y intercept, but not the slope of the line.

The present invention is particularly useful in patients with heart failure, or with cardiomyopathies leading to heart failure.

By the term "manganese contrast agent" is meant herein an agent which comprises at least one manganese atom or ion. The manganese contrast agents for use in a method according to the invention may be obtained commercially or prepared using any procedure known to the person skilled in the art. The manganese contrast agent may be in the form of an ionic or more preferably a non-ionic complex. Especially preferred in the uses and methods of the invention are manganese chelate complexes. The complexes may be bound to one or more carrier molecules.

A wide range of suitable manganese chelators, including macromolecule-bound manganese chelators, are known in the art. Manganese (II) chelates with dipyridoxyl chelating agents are particularly preferred for the uses and methods of the present invention.

In some embodiments, a manganese chelator of formula (I), or a pharmaceutically acceptable salt thereof, is used. As used herein, the term "pharmaceutically acceptable" means that compound must be physiologically acceptable to the recipient as well as, if part of a composition, compatible with other ingredients of the composition.

(I)

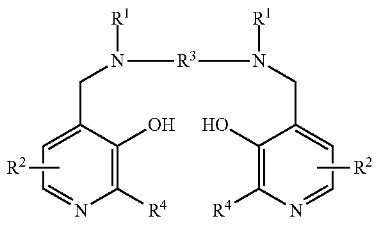

wherein in formula I each $R^1$ independently represents hydrogen or $-CH_2COR_5$;

$R^5$ represents hydroxy, optionally hydroxylated alkoxy, amino or alkylamido;

each $R^2$ independently represents a group $XYR^6$;

X represents a bond, or a $C_{1-3}$ alkylene or oxoalkylene group optionally substituted by a group $R^7$;

Y represents a bond, an oxygen atom or a group $NR^6$;

$R^6$ is a hydrogen atom, a hydroxyl group, a group $COOR^8$, a group $OP(O)(OR^8)R^7$, a group $OP(O)(OM)R^7$ or an alkyl, alkenyl, cycloalkyl, aryl or aralkyl group optionally substituted by one or more groups selected from $COOR^8$, $CONR^8_2$, $NR^8_2$, $OR^8$, $=NR^8$, $=O$, $OP(O)(OR^8)R^7$, $OP(O)(OM)R^7$ and $OSO_3M$;

$R^7$ is OM, hydroxy, an optionally hydroxylated, optionally alkoxylated alkyl or aminoalkyl group;

$R^8$ is a hydrogen atom, or an optionally hydroxylated, optionally alkoxylated alkyl group;

M is a hydrogen atom or one equivalent of a physiologically tolerable cation, e.g. an alkali or alkaline earth cation (e.g. $Na^+$), an ammonium ion or an organic amine cation, such as a meglumine ion;

$R^3$ represents a $C_{1-8}$ alkylene group, preferably a $C_{1-6}$, e.g. a $C_{2-4}$ alkylene group, a 1,2-cycloalkylene group, or a 1,2-arylene group; and each $R^4$ independently represents hydrogen or $C_{1-3}$ alkyl.

As used herein the terms "alkyl" and "alkylene" include both straight-chained and branched, saturated and unsaturated hydrocarbons. The term "1,2-cycloalkylene" includes both cis and trans cycloalkylene groups and alkyl substituted cycloalkylene groups having from 5-8 carbon atoms. The term "1,2-arylene" includes phenyl and napthyl groups and alkyl substituted derivatives thereof having from 6 to 10 carbon atoms. The compounds may contain one or more chiral centres and/or double bonds, and may therefore exist in different stereoisomeric forms, such as double-bond isomers (i.e., geometric isomers), enantiomers, and/or diastereomers. It is to be understood that both stereomerically pure forms (e.g., geometrically pure, enantiomerically pure, or diastereomerically pure) and stereoisomeric mixtures are encompassed in the invention. The invention is considered to extend to diastereomers and enantiomers, as well as racemic mixtures. Compounds herein described may be resolved into their geometric isomers, enantiomers and/or diastereomers, using methods known in the art.

As used herein, the terms straight chain and branched alkyl, alkenyl, alkoxy comprise all such substituents of a given chain length, including substituents that are cyclic or comprise a cycle. Unless otherwise specified, any alkyl, alkylene or alkenyl moiety may conveniently contain from 1 to 20, preferably 1-8, more preferably 1-6 and especially preferably 1-4 carbon atoms.

Cycloalkyl, aryl and aralkyl moieties may conveniently contain 3-18, preferably 5-12 and especially preferably 5-8 ring atoms. Aryl moieties comprising phenyl or naphthyl groups are preferred. As aralkyl groups, phenyl $C_{1-3}$ alkyl, especially benzyl, are preferred.

Where groups may optionally be substituted by hydroxy groups, this may be monosubstitution or polysubstitution and, in the case of polysubstitution, alkoxy and/or hydroxy substituents may be carried by alkoxy substituents.

Particularly preferred chelates are manganese chelates of a compound of formula II and pharmaceutically acceptable salts thereof, (II)

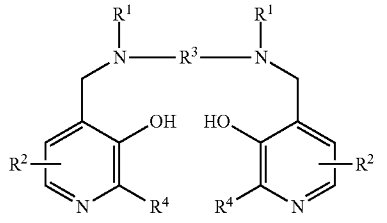

wherein in formula II each $R^1$ independently represents hydrogen or $—CH_2COR_5$;

$R^5$ represents hydroxy, optionally hydroxylated alkoxy, amino or alkylamido;

each $R^2$ independently represents an alkyl group (e.g. a $C_{1-6}$ alkyl group) substituted by one or more groups selected from hydroxyl, $COOR^3$, $CONR^8_2$, $NR^8_2$, $OR_3$, $=NR^8$, $=O$, $OP(O)(OR_3)R^7$, $OP(O)(OM)R^7$ and $OSO_3M$;

$R^7$ is OM, hydroxy, an optionally hydroxylated, optionally alkoxylated alkyl or aminoalkyl group;

$R^8$ is a hydrogen atom, or an optionally hydroxylated, optionally alkoxylated alkyl group;

M is a hydrogen atom or one equivalent of a physiologically tolerable cation, e.g. an alkali or alkaline earth cation (e.g. $Na^+$), an ammonium ion or an organic amine cation, such as a meglumine ion;

$R^3$ represents a $C_{1-3}$ alkylene group, preferably a $C_{1-6}$, e.g. a $C_{2-4}$ alkylene group; and each $R^4$ independently represents hydrogen or $C_{1-3}$ alkyl.

In formula II, $R^5$ is preferably hydroxy. Preferably each group $R^1$ represents $—CH_2COR_5$ in which $R^5$ is hydroxy.

In further preferred compounds of formula II, $R^3$ is preferably ethylene (i.e. $—CH_2—CH_2—$). In further preferred compounds each $R^4$ is $C_{1-3}$ alkyl, especially methyl.

The compounds of formula II may have the same or different $R^2$ groups on the two pyridyl rings and these may be attached at the same or different ring positions. However, it is especially preferred that substitution be at the 5- and 6-positions, most especially the 6-position, i.e. para to the hydroxy group. Compounds in which the $R^2$ groups are identical and identically located, e.g. 6,6', are especially preferred.

In the compounds of formula II, $R^2$ is preferably a $C_{1-4}$, e.g. $C_{1-2}$ alkyl group. More preferably $R^2$ is $C_1$. Preferred substituents on $R^2$ are hydroxyl, $OP(O)(OR^8)R^7$ and $OP(O)(OM)R^7$. $R^7$ is preferably a hydroxyl group or OM. $R^3$ is preferably hydrogen.

Particularly preferred identities for group $R^2$ include $CH_2OP(O)(OM)OM$, $CH_2OP(O)(OM)OH$, $CH_2OP(O)(OH)_2$ or $CH_2OH$ groups. Compounds of formula II in which $R^3$ is ethylene and $R^2$ has any of the identities listed above are particularly preferred.

Especially preferred is the manganese (II) chelate of N,N'-bis-(pyridoxal-5-phosphate)-ethylenediamine-N,N'-diacetic acid (MnDPDP). MnDPDP is also known as manganese (II) N,N'-dipyridoxyl-ethylenediamine-N,N'-diacetate-5,5'-bis(phosphate) and as mangafodipir trisodium.

A contributing factor to $R^1$ enhancement by manganese in MEMRI is strong protein binding of the released manganese causing a reduced tumbling rate and a 20 fold increase in relaxivity compared to free manganese. This increased efficacy lowers the dose necessary for the MRI, thus reducing the risk of cardiotoxicity.

Also preferred is the manganese (II) chelate of N,N'-dipyridoxyl-thylenediamine-N,N'-diacetic acid (MnPLED). MnPLED is also known as manganese (II) N,N-dipyridoxyl-ethylenediamine-N,N'-diacetate. Also preferred is the manganese (II) chelate of N-pyridoxyl, N'-(pyridoxyl-5-phosphate)-ethylenediamine-N—N'-diacetic acid (MnDPMP). MnDPMP is also known as manganese (II) N,N'-dipyridoxyl-ethylenediamine-N,N'-diacetate-5-phosphate.

As will be understood, any of the compounds herein described may be provided in the form of a pharmaceutically acceptable salt or solvate thereof. Procedures for salt formation and solvate formation are conventional in the art.

The compounds for use in the methods of the invention may be commercially available or may be prepared by any procedure known to the skilled person. Such procedures are well-known in the art.

Where the metal chelate carries an overall charge it will conveniently be used in the form of a salt with one or more pharmaceutically acceptable counterions. Non-limiting examples of such counterions include ammonium, substituted ammonium, alkali metal or alkaline earth metal cation or an anion deriving from an inorganic or organic acid. The counterion may be a calcium cation. The counterion may be meglumine.

In the methods and uses of the invention, the manganese contrast agent is preferably formulated into a pharmaceutical composition. As used herein, the term "composition" refers to a mixture, in any formulation, of one or more manganese contrast agents with one or more additional chemical component.

The composition may further include one or more of any conventional, pharmaceutically acceptable excipients and/or carriers, e.g. osmolality adjusting agents, solvents, fillers, diluents, binders, viscosity modifiers, surfactants, dispersing agents, disintegration agents, emulsifying agents, wetting agents, suspending agents, thickeners, buffers, pH modifiers, absorption-delaying agents, stabilisers, antioxidants, preservatives, antifungal agents, antimicrobial agents, chelating agents, adjuvants, and/or other additives. Representative examples of suitable additives include physiologically biocompatible buffers (e.g. DTPA or DTPA bisamide), calcium chelate complexes (e.g. calcium DTPA salts, calcium DTPA-bisamide salts or NaCaDTPA bisamide) or additions (e.g. 1 to 50 mole percent) of calcium or sodium salts (e.g. calcium chloride, calcium ascorbate, calcium gluconate or calcium lactate). Conventional formulation techniques known in the art, e.g., conventional mixing, dissolving, suspending, levigating, emulsifying, entrapping or compressing processes, may be used to formulate the composition.

Preferred compositions for the methods and uses of the invention are in a form suitable for injection or infusion directly or after dispersion in or dilution with a physiologically acceptable carrier medium, e.g. water for injections.

Thus, although the contrast agents may be in a solid form, solutions, suspensions and dispersions in a physiologically acceptable carrier is generally preferred.

The compositions should be free from physiologically unacceptable agents. The compositions should be substantially free of contaminants and/or impurities. Preferably, the compositions have low osmolality, so that irritation and/or other adverse effects upon administration are minimised. The compositions are preferably isotonic or slightly hypertonic. Hence, preferred carriers and/or diluents include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405 1412 and 1461 1487 (1975) and The National Formulary XIV, 14th ed. Washington: American Pharmaceutical Association (1975).

The compositions employed in the uses and methods of the invention should be sterile. Sterilisation can be achieved by any suitable method, including but not limited to by applying heat, chemicals, irradiation, high pressure, filtration, or combinations thereof.

For effective uptake by the calcium channels in the cardiomycytes, the manganese is preferably in the state $Mn^{2+}$. To inhibit oxidation to $Mn^{3+}$, the compositions employed in the uses and methods of the invention may contain an antioxidant, e.g. ascorbic acid or a reducing sugar.

The concentration of the manganese contrast agents in the compositions of the present disclosure will vary depending on several factors including the nature of the compound and/or the composition. Preferably, however, concentration ranges of 0.001 to 1 mmol/ml, more preferably 0.005 to 0.1 mmol/ml, still more preferably 0.01 to 0.05 mmol/ml, e.g. about 0.05 mmol/ml compound is used.

Suitable compositions for application in the methods and uses of the invention may be obtained commercially or prepared using any procedure known to the person skilled in the art.

In another aspect, the invention relates to a computer-implemented method of determining a cellular manganese uptake rate in a subject. In one embodiment, the invention relates to a computer-implemented method of determining a cardiomyocyte cellular manganese uptake rate in a subject, the method comprising the steps of i) receiving from the PACS system of an MRI instrument scan data from a first longitudinal relaxation time measurement $T1_{blood}(0)$ of blood of the subject and data from a first longitudinal relaxation time measurement $T1_{myocardium}(0)$ of the myocardium of the subject, performed for a section of the heart of the subject;

ii) receiving from the PACS system of an MRI instrument series of scan data from one or more measurements $T1_{blood}(t_i)$ of the longitudinal relaxation time of the blood of the subject and one or more measurements $T1_{myocardium}(t_i)$ of the longitudinal relaxation time of the myocardium of the subject, performed for said section of the heart of the subject, wherein the $T1_{blood}(t_i)$ measurements and the $T1_{myocardium}(t_i)$ measurements have been performed at one or more time points $t_i$ during administration to the subject of a dose $d_a$ of a contrast agent at a dosing rate of $D_a$ μmol/kg/min, the contrast agent comprising a manganese contrast agent having a stability constant of 10-18, or a pharmaceutically acceptable salt thereof, the administration being completed at a time $t_a$, iii) receiving from the PACS system of an MRI instrument pulse sequence series data from one or more measurements $T1_{blood}(t_i)$ of the longitudinal relaxation time of the blood of the subject and from one or more measurements $T1_{myocardium}(t_i)$ of the longitudinal relaxation time of the myocardium of the subject, performed for said section of the heart of the subject, wherein the measurements have been performed at one or more time points $t_i$ up to 60 minutes after $t_a$;

iv) calculating the change in myocardial relaxation rate $\Delta R1_{myocard}(t_i)$ for each of the time points $t_i$ of steps i), ii) and iii) according to the formula $$\Delta R1_{myocard}(t_i) = \frac{1}{T1_{myocard}(t_i)} - \frac{1}{T1_{myocard}(0)};$$

v) receiving a haematocrit value, hct, for the subject;

vi) calculating the change in plasma relaxation rate $\Delta R1_{plasma}(t_i)$ for each of the time points $t_i$ of steps i), ii) and iii) according to the formula $$\Delta R1plasma(t_i) = \frac{\frac{1}{T1_{blood}(t_i)} - \frac{1}{T1_{blood}(0)}}{1 - hct};$$

vii) estimating the integrals $$\int_0^{t_i} \Delta R1_{plasma}(t)dt$$

using each $\Delta R1_{plasma}(t_i)$ value of step vi);

viii) receiving an estimate of the ECV for said section of the heart of the subject;

ix) defining an equation for a straight line y=A+Bx, wherein $$y = \frac{\Delta R1myocardium(t)}{\Delta R1plasma(t)},$$

$A=K_{ECF}$*ECV, wherein $K_{ECF}$ is a constant, $$B = K_{cell}^{\Delta R1} * K_{ECF}$$

and $$x = \frac{(1 - ECV) * K_{ECF} * \int_0^t \Delta R1plasma(t)dt}{\Delta R1plasma(t)};$$

x) estimating the slope B, and thus the cardiomyocyte cellular manganese uptake rate $$K_{cell}^{Mn} * K_{ECF} = B,$$

by a linear regression method with forced intercept $A=K_{ECF}*ECV$.

In another aspect, the invention relates to a data processing apparatus comprising means for carrying out said computer-implemented method of determining a cellular manganese uptake rate in a subject. The apparatus may be, for example, any one or more of a personal computer (PC), a tablet computer, a server device, a mobile device, a smart phone, a tablet device, a workstation, a personal digital assistant (PDA), a portable media player (PMP), an augmented reality (AR) device, an internet-of-things (IoT) device, a robotics device, and an apparatus for use in specific processing, such as a medical diagnosis apparatus. In one embodiment, the invention relates to a data processing apparatus comprising means for carrying out said computer-implemented method of determining a cardiomyocyte cellular manganese uptake rate in a subject.

The apparatus may be communicably connected to the MRI equipment used to obtain the T1 MRI data sets via a cable or a communication network. The MRI equipment used to obtain the T1 MRI data sets may comprise the apparatus.

In another aspect, the invention relates to a computer program comprising instructions which, when the program is executed by a computer, cause the computer to carry out said computer-implemented method of determining a cellular manganese uptake rate in a subject. Such a computer program may, for example, be an operating system, a software application, an interface and so on. The computer program is suitable for running on a computer system, at least including code portions for performing steps of a method according to the invention when run on a computer or computer system. Such a computer program may, for example, be provided on a data carrier, or stored with data loadable in a memory of a computer system, the data representing the computer program. The computer program may, for example, be a software application or a subcomponent of a software application. In one embodiment, the invention relates to a computer program comprising instructions which, when the program is executed by a computer, cause the computer to carry out said computer-implemented method of determining a cardiomyocyte cellular manganese uptake rate in a subject.

In yet another aspect, the invention relates to a computer-readable medium having stored thereon said computer program. The computer-readable medium may be, for example, an electrical connection having two or more wires, a portable computer diskette such as a floppy disk or a flexible disk, magnetic tape or any other magnetic medium, a hard disk, a random access memory (RAM), a read-only memory (ROM), an erasable programmable read-only memory (EPROM or Flash memory), a memory card, any other memory chip or cartridge, an optical fiber, a portable compact disc read-only memory (CD-ROM), any other optical medium, any physical medium with patterns of holes, or any other medium from which a computer can read, or any suitable combination of the foregoing. In a further aspect, the invention provides a method of diagnosing heart failure in a subject.

In a further aspect, the invention provides the use of a manganese contrast agent, or a pharmaceutically acceptable salt thereof, for determining the cardiomyocyte cellular manganese uptake rate of a subject.

In a further aspect, the invention provides the use of a manganese contrast agent, or a pharmaceutically acceptable salt thereof, for determining the cardiomyocyte cellular calcium uptake rate of a subject.

The embodiments and features described in the context of one aspect of the invention, e.g. for the method for determining the cardiomyocyte cellular manganese uptake rate of a subject, also apply to the other aspects of the invention, e.g. the method for in vivo diagnosis of heart failure in a subject.

The invention shall not be limited to the shown embodiments and examples. While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is to be understood that various alternatives to the embodiments described herein can be employed in practicing the disclosure.

It is to be understood that every embodiment of the disclosure can optionally be combined with any one or more of the other embodiments described herein.

It is to be understood that each component, compound, or parameter disclosed herein is to be interpreted as being disclosed for use alone or in combination with one or more of each and every other component, compound, or parameter disclosed herein. It is further to be understood that each amount/value or range of amounts/values for each component, compound, or parameter disclosed herein is to be interpreted as also being disclosed in combination with each amount/value or range of amounts/values disclosed for any other component(s), compound(s), or parameter(s) disclosed herein, and that any combination of amounts/values or ranges of amounts/values for two or more component(s), compound(s), or parameter(s) disclosed herein are thus also disclosed in combination with each other for the purposes of this description. Any and all features described herein, and combinations of such features, are included within the scope of the present invention provided that the features are not mutually inconsistent.

It is to be understood that each lower limit of each range disclosed herein is to be interpreted as disclosed in combination with each upper limit of each range disclosed herein for the same component, compound, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, or parameter disclosed in the description or an example is to be interpreted as a disclosure of either a lower or an upper limit of a range and thus can be combined with any other lower or upper limit or a range or specific amount/value for the same component, compound, or parameter disclosed elsewhere in the application to form a range for that component, compound, or parameter.

EXAMPLES

Example 1: T1 Mapping of Blood and Myocardium

T1 mapping MRI was performed in a healthy volunteer to obtain baseline T1 values for the blood and myocardium before infusion of MnDPDP. A midventricular short axis view was used and a region of interest in the left ventricle myocardium and a region of interest in the blood in the ventricular cavity were used for measurements. An infusion of MnDPDP was administered at a rate of 50 μmol/min until a dose of 5 μmol/kg body weight was administered. The total infusion time was 7.5 minutes. T1 mapping MRI was performed every 2.5 minutes for a total of 40 minutes to collect data for kinetic analysis.

Figure 3:
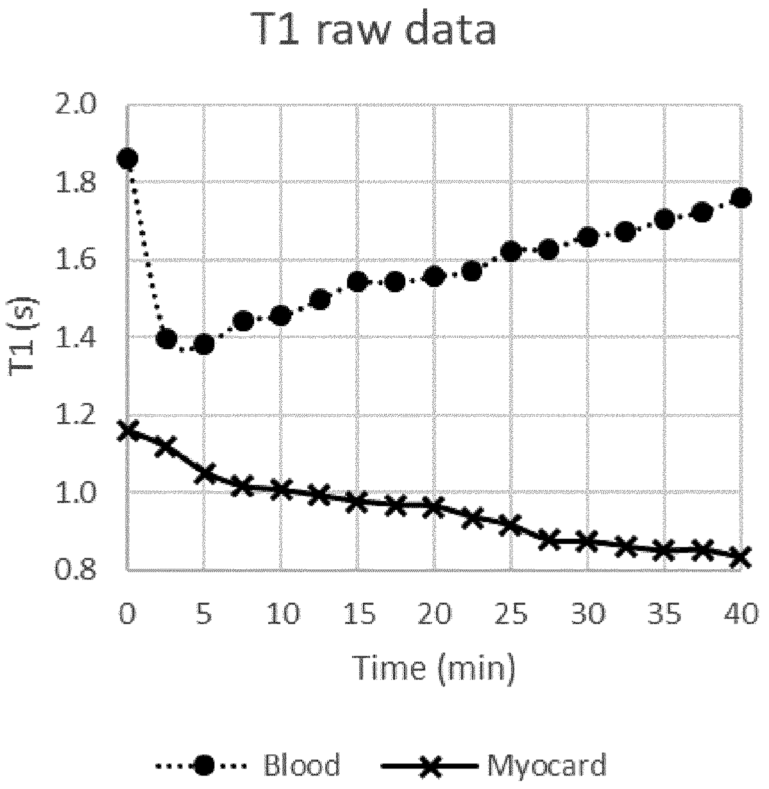
FIG. 3 shows blood and myocardium T1 values for a healthy volunteer.

FIG. 3 shows the blood and myocard T1 values measured. There was a rapid reduction of blood T1 until the end of infusion, whereafter the blood T1 slowly increased to normal. The myocardial T1 showed a continued reduction during the 40 minutes examination, due to the irreversible nature of manganese uptake.

After the examination, the myocardial T1 values were converted to changes in relaxation rates from the baseline values according to equation 12. The heamocrit for the subject was measured to 0.41 and the plasma T1 values were converted to changes in relaxation rates according to equation 13.

Figure 4:
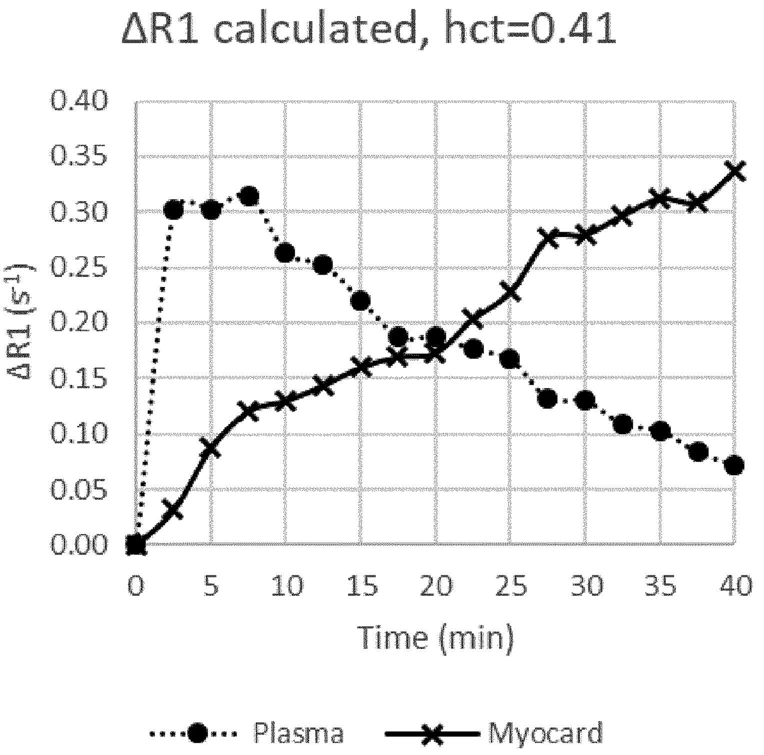
FIG. 4 shows plasma and myocardium changes in relaxation rates for a healthy volunteer.

FIG. 4 shows the myocard and plasma changes in relaxation rates during the examination. The plasma ΔR1 value is highest after 7.5 minutes, corresponding to the end of the infusion, and declined with a halftime of approximately 15 minutes. The myocardial ΔR1 value continued to increase for the entire examination.

The integral of the plasma relaxation rate was measured for each time point using the trapezoidal method according to equation 16.

The ECV of the myocardium had been measured to 0.25 a week before the examination. The rate constant for cardiomyocyte intracellular relaxivity increase $$K_{cell}^{\Delta R1},$$

and thus the cardiomyocyte cellular manganese uptake rate $$K_{cell}^{Mn},$$

was calculated according to equation 20 where the constant $K_{ECF}$ was set equal to 1. The $$K_{cell}^{Mn}$$

value was 0.0591 $min^{-1}$. The data used to calculate the rate constant is shown graphically in FIG. 5 ("ict"), corresponding to a straight line with $$\text{slope} = K_{cell}^{Mn} = 0.0591\ \text{min}^{-1}$$

and intercept=ECV=0.25.

Figure 5:
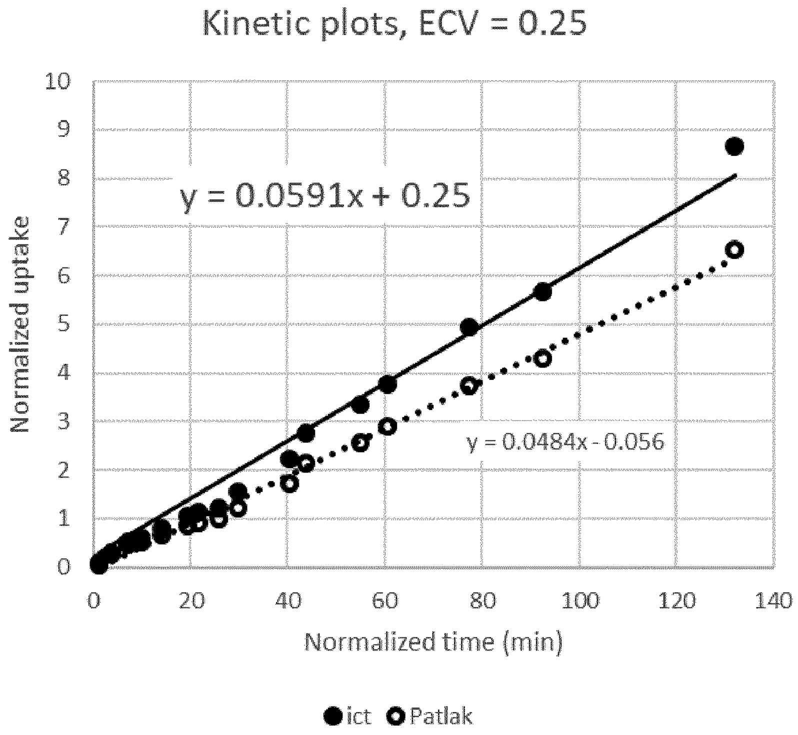
FIG. 5 shows a graphical representation of the kinetic analysis (ict) compared to the prior art Patlak method for a healthy volunteer.

For comparison, the Patlak plot constructed with the method described in the prior art is also shown in FIG. 5 ("Patlak"). It is observed that the intercept of the Patlak curve is −0.056, which cannot be a measure of ECV or any other compartment since the number is negative. It is also observed that the slope of the Patlak line, 0.0484 $min^{-1}$, is lower than the correct value since the Patlak data does not take into account that a region of interest in the myocardium contains tissue elements other than cardiomyocytes.

Example 2: T1 Mapping of Cardiomyopathia Patient

T1 mapping MRI was performed in a patient with a diagnosis of dilated cardiomyopathia to obtain baseline T1 values for the blood and myocardium before infusion of MnDPDP. A midventricular short axis view was used and a region of interest in the left ventricle myocardium and a region of interest in the blood in the ventricular cavity was used for measurements. An infusion of MnDPDP was administered at a rate of 50 μmol/min until a dose of 5 μmol/kg body weight was administered. The total infusion time was 7.5 minutes. T1 mapping MRI was performed every 2.5 minutes for a total of 40 minutes to collect data for kinetic analysis.

Figure 6:
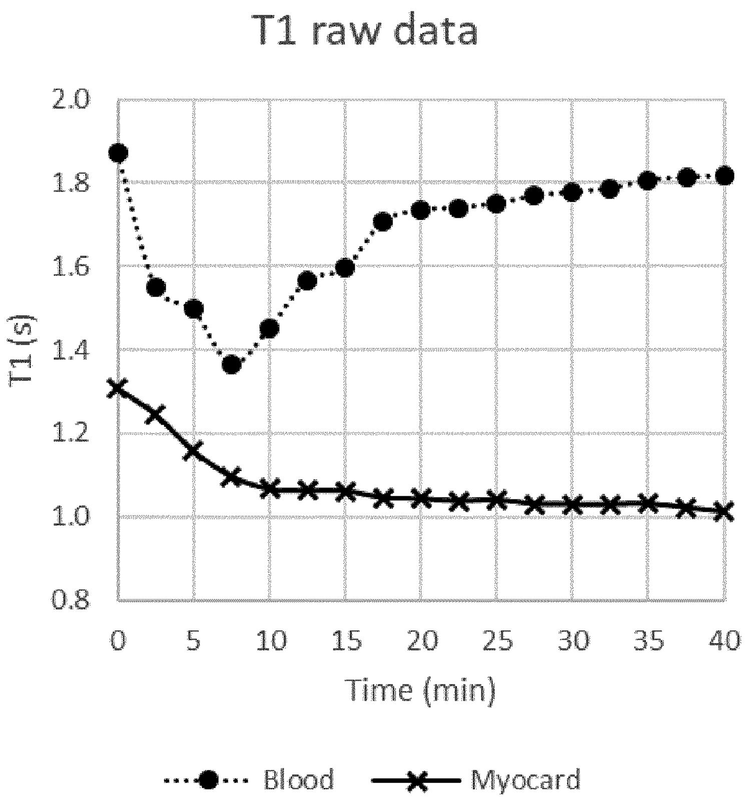
FIG. 6 shows blood and myocardium T1 values for a patient diagnosed with dilated cardiomyopathy.

FIG. 6 shows the blood and myocard T1 values measured. There was a rapid reduction of blood T1 until the end of infusion, whereafter the blood T1 slowly increased. The myocardial T1 showed a continued reduction during the 40 minutes examination.

After the examination, the myocardial T1 values were converted to changes in relaxation rates from the baseline values according to equation 12. The heamocrit for the subject was measured to 0.44 and the plasma T1 values were converted to changes in relaxation rates according to equation 13.

Figure 7:
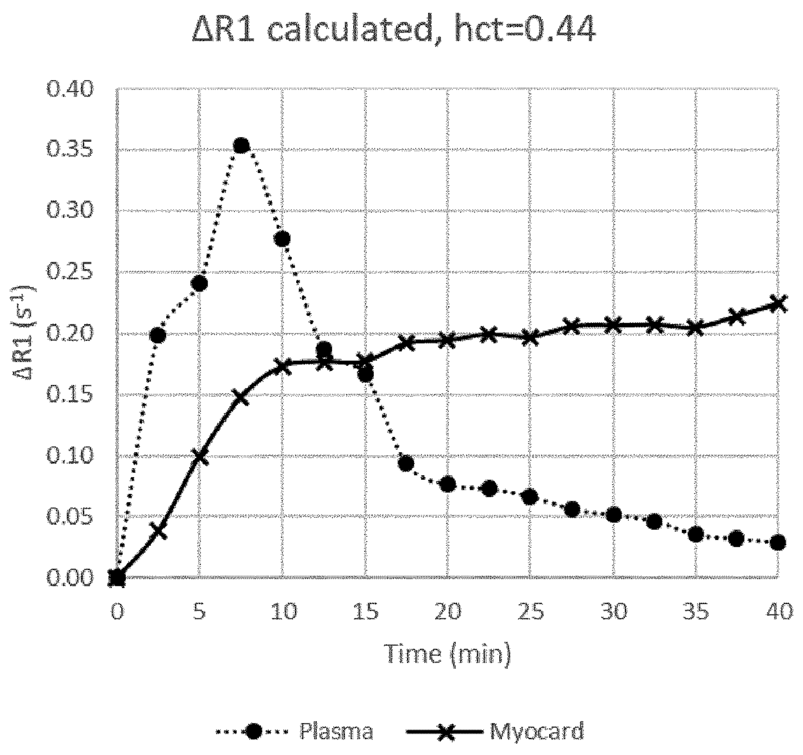
FIG. 7 shows plasma and myocardium changes in relaxation rates for a patient diagnosed with dilated cardiomyopathy.

FIG. 7 shows the calculated myocard and plasma changes in longitudinal relaxation rates during the examination. The plasma ΔR1 value was highest after 7.5 minutes, corresponding to the end of the infusion, and declined with a halftime of approximately 12 minutes. The myocardial ΔR1 value continued to increase during the entire examination.

The integral of the plasma relaxation rate was measured for each time point using the trapezoidal method according to equation 16.

The extracellular volume fraction of the myocardium had been measured to 0.35 a week before the examination. This value is higher than normal, and 0.10 higher than that for the healthy volunteer presented in Example 1, an indication that there was a (75−65)/75=13% lower fraction of cardiomyocytes in the myocardium of this patient compared to the healthy volunteer. A loss of cardiomyocytes will lead to a reduction of manganese-related myocardial relaxation rate if the remaining cells are functioning normally.

The kinetic analysis performed with the Patlak method of prior art estimates the uptake rate constant to 0.0429, which is 11.4% lower than for the healthy volunteer. This is what would be expected from the loss of cells without a loss of individual cell function. Thus, by applying the prior art method, it would therefore wrongly be concluded that the cellular manganese flux rate was reduced.

The rate constant for cardiomyocyte intracellular relaxivity increase $$K_{cell}^{\Delta R1},$$

and thus the cardiomyocyte cellular manganese uptake rate $$K_{cell}^{Mn},$$

was calculated according to the invention, applying equation 20 where the constant $K_{ECF}$ was set equal to 1. The $$K_{cell}^{Mn}$$

value was 0.0650 $min^{-1}$. The data used to calculate the rate constant is shown graphically in FIG. 8 ("ict"), corresponding to a straight line with $$\text{slope} = K_{cell}^{Mn} = 0.0650\ \text{min}^{-1}$$

and intercept=ECV=0.35.

Figure 8:
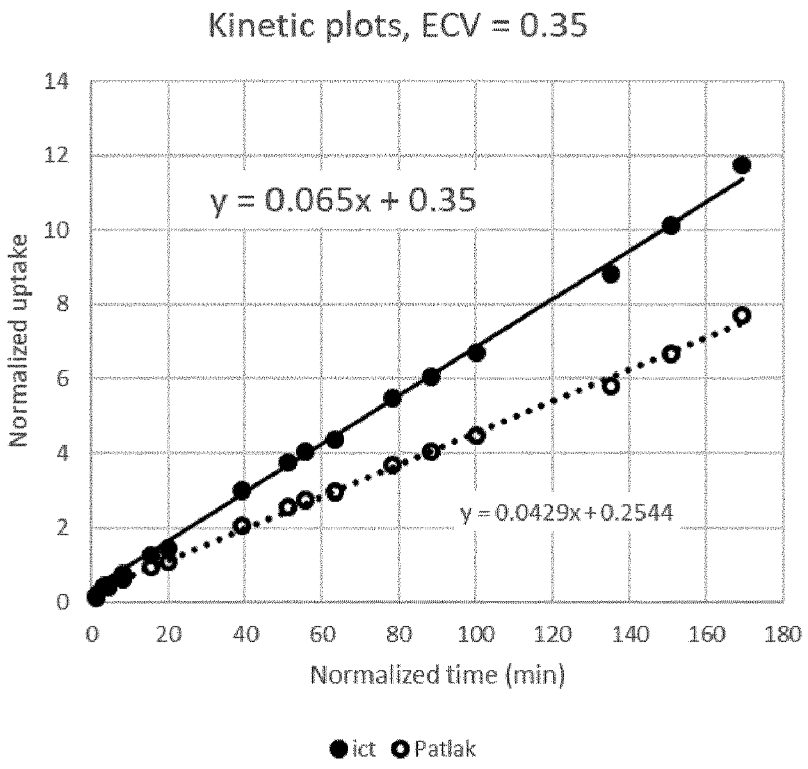
FIG. 8 shows a graphical representation of kinetic analysis (ict) compared to the prior art Patlak method for a patient diagnosed with dilated cardiomyopathy.

For comparison, the Patlak plot constructed with the method described in the prior art is also shown in FIG. 8 ("Patlak"). The estimate of the cellular uptake rate constant according to the invention is higher in this patient than in the healthy volunteer, which may be an indication that there is a compensatory increased activity in the remaining cells. This is the opposite conclusion compared to that of the Patlak method, and would lead to different recommended therapeutic decisions.

Example 3: Determination of Cardiomyocyte Cellular Manganese Uptake Rate in Patients with Hypertrophic Cardiomyopathy, Including Determination of the Ratio Between Manganese Concentration in ECF and Plasma T1 mapping data from 5 patients with hypertrophic cardiomyopathia was averaged to obtain average baseline T1 values for blood and myocardium before infusion of MnDPDP. A midventricular short axis view was used in each patient and a region of interest in the left ventricle myocardium and a region of interest in the blood in the ventricular cavity was used for measurements. An infusion of MnDPDP was administered at a rate of 50 μmol/min until a dose of 5 μmol/kg body weight was administered. The total infusion time was 7.5 minutes. T1 mapping MRI was performed every 2.5 minutes for a total of 40 minutes to collect data for kinetic analysis.

Figure 9:
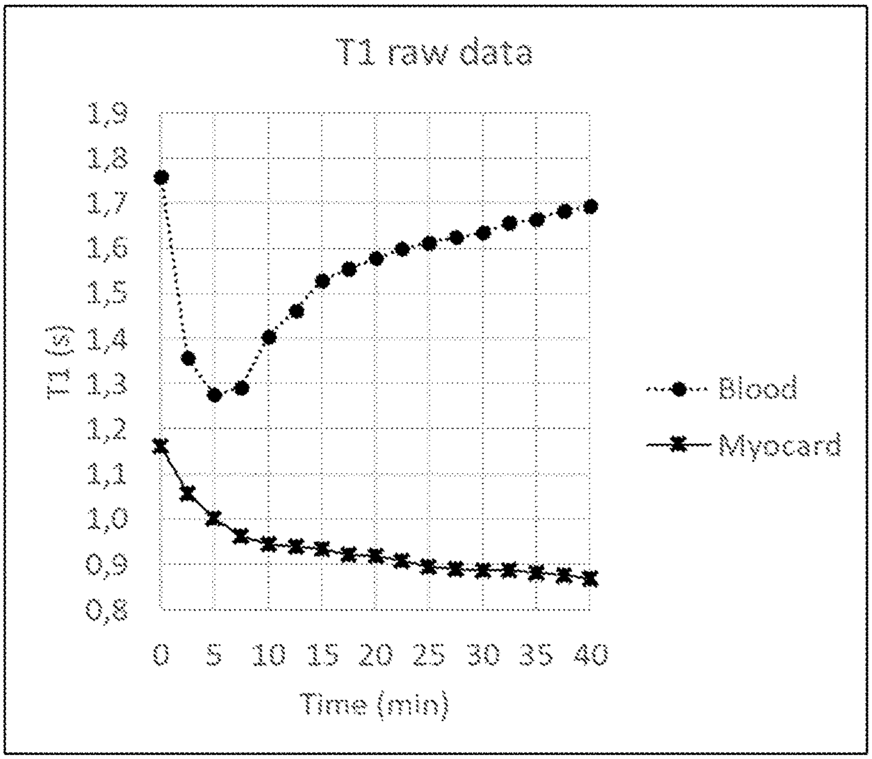
FIG. 9 shows average blood and myocardium T1 values for a group of 5 patients diagnosed with hypertrophic cardiomyopathy.

FIG. 9 shows the average blood and myocard T1 values measured. There was a rapid reduction of blood T1 until the end of infusion, whereafter the blood T1 slowly increased. The myocardial T1 showed a continued reduction during the 40 minutes examination.

After the examinations, the myocardial T1 values were converted to changes in relaxation rates from the baseline values according to equation 12. The average heamocrit for the 5 subjects was measured to 0.416 and the plasma T1 values were converted to changes in relaxation rates according to equation 13.

Figure 10:
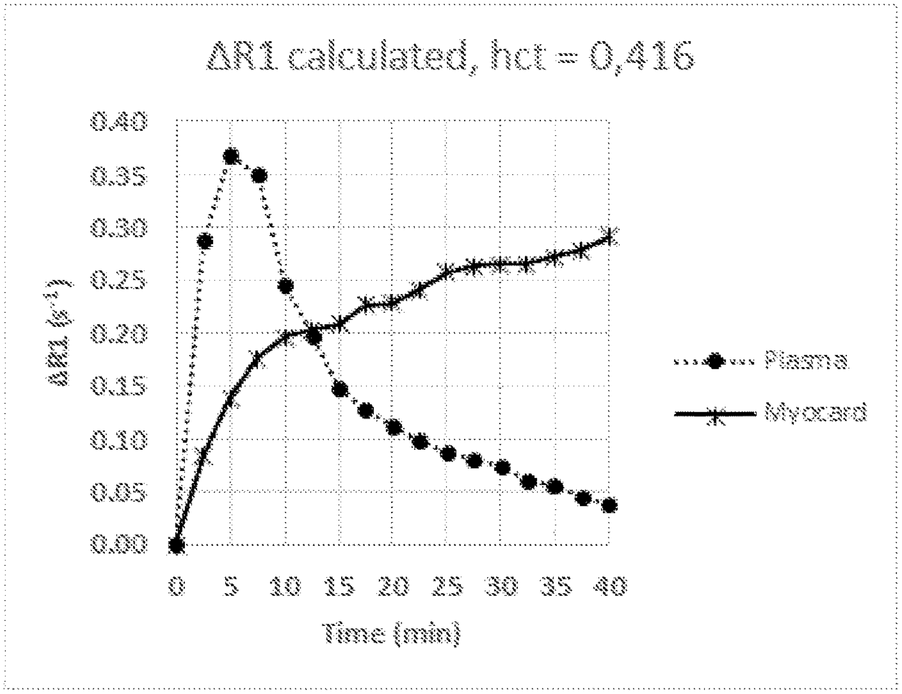
FIG. 10 shows average plasma and myocardium changes in relaxation rates for a group of 5 patients diagnosed with hypertrophic cardiomyopathy.

FIG. 10 shows the calculated myocard and plasma changes in longitudinal relaxation rates during the examination. The plasma ΔR1 value was highest after 7.5 minutes, corresponding to the end of the infusion, and declined with a halftime of approximately 12 minutes. The myocardial ΔR1 value continued to increase during the entire examination.

The integral of the plasma relaxation rate was measured for each time point using the trapezoidal method according to equation 16.

In each patient the extracellular volume fraction of the myocardium had been measured a week before the examination and the average was 0.322.

Figure 11:
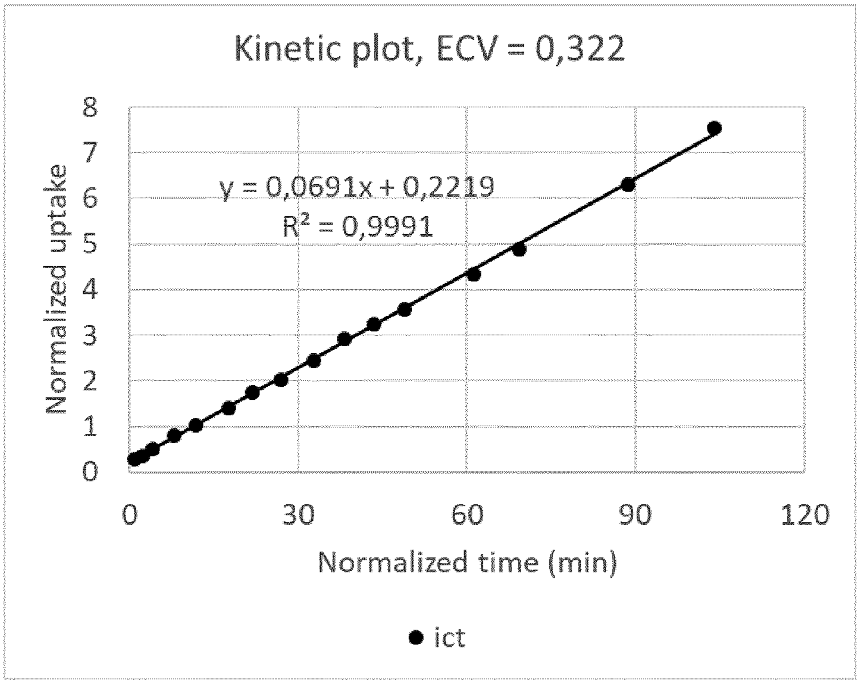
FIG. 11 shows a graphical representation of kinetic analysis (ict) for a group of 5 patients diagnosed with hypertrophic cardiomyopathy.

When data from a group of subjects are averaged, the random errors in the measurements are minimized and tend to cancel, so the linear regression analysis was performed without restrictions to the intercept. The results are presented in FIG. 11. The equation describing the linearized data was $$\frac{\Delta R1 myocardium(t)}{\Delta R1 plasma(t)} = 0.2219 + 0.0691 * (1 - 0.322) * \frac{\int_0^t \Delta R1 plasma(t)dt}{\Delta R1 plasma(t)}$$

This analysis gives a near exact representation of the data with a $R^2$ of 0.9991.

Figure 12:
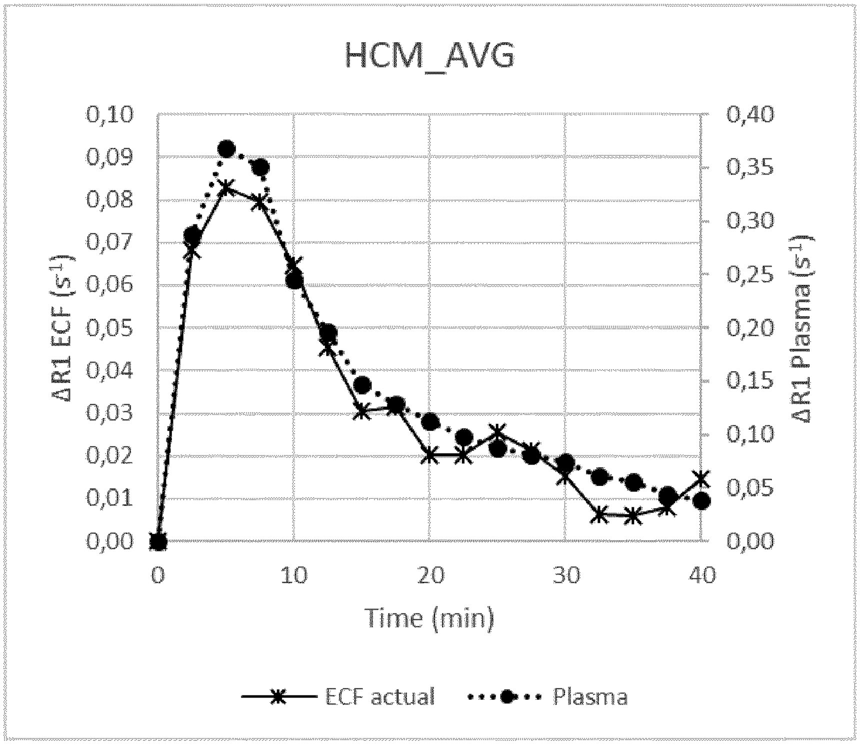
FIG. 12 shows the difference between total and irreversible myocardial relaxation rates, ΔR1 ECF, and the change in plasma relaxation rates for a group of 5 patients diagnosed with hypertrophic cardiomyopathy.
Figure 13:
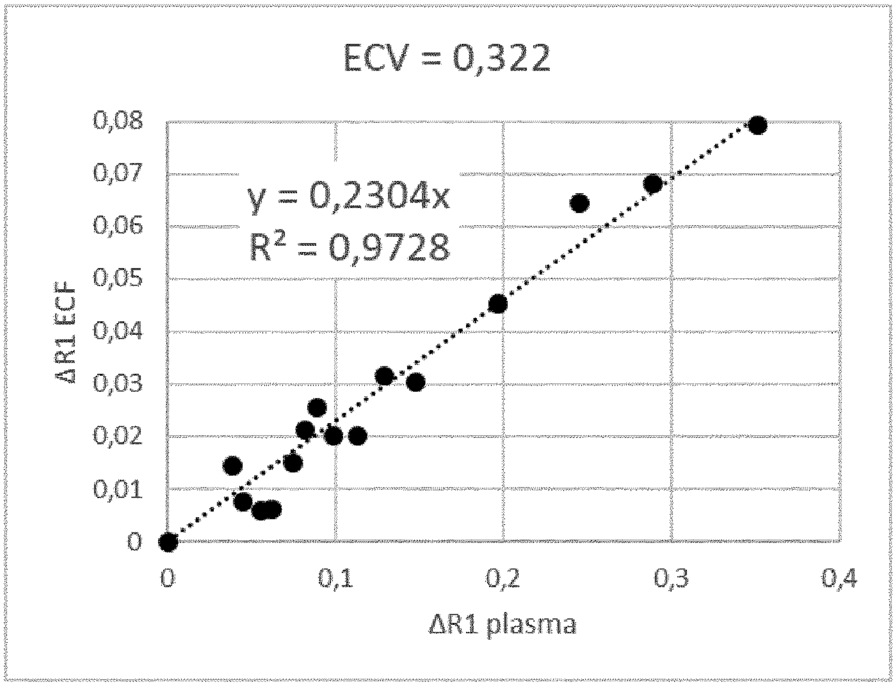
FIG. 13 shows the correlation between ΔR1 ECF and ΔR1 Plasma for a group of 5 patients diagnosed with hypertrophic cardiomyopathy.
Figure 14:
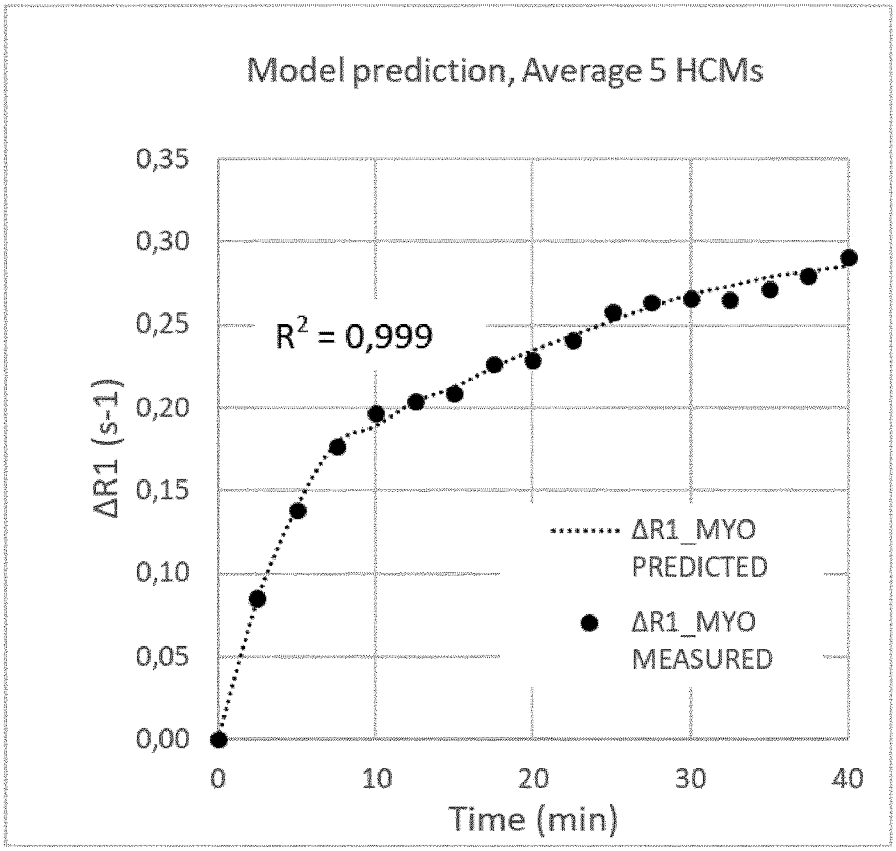
FIG. 14 shows the measured changes in myocardial relaxation rates and the model predictions calculated according to the invented method.

Determination of the Constant $K_{ECF}$:

A more detailed analysis of the reversible component of the data was performed by subtracting the predicted irreversible ΔR1 from the actual measured total myocardial ΔR1. The result is presented in FIG. 12 together with the curve describing ΔR1 in plasma. Surprisingly, there is no time shift between the peak plasma value and the peak ECF value. This allows a calculation of the constant ratio between the manganese concentration in ECF and plasma from the slope of the curve where Y=ΔR1 ECF and X=ΔR1 plasma as shown in FIG. 13.

If the ECF was in equilibrium with plasma, the slope would be the ECV=0.322. However, due to the uptake of manganese into the cardiomyocytes, the ECF is in dynamic equilibrium with plasma with a manganese concentration ratio of $$\frac{\Delta R1\ ECF}{\Delta R1\ \text{plasma} * ECV} = K_{ECF} = 0.2304/0.322 = 0.72.$$

Reference is made to FIG. 1 which shows that when the manganese concentration in the ECF is in dynamic equilibrium, $K_{ECF}$=K1/(K2+K3). Assuming that the rate constant for diffusion between plasma and the ECF is the same in both directions, K1=K2 and K3/K1=1/$K_{ECF}$−1=1/0.72−1=0.40. This analysis shows that the rate constant for irreversible uptake in this case is 40% of the rate constant for diffusion between plasma and the ECF.

When the ratio between the manganese concentration in the ECF and plasma can be estimated, the apparent cellular rate constant $$K_{cell}^{Mn} * K_{ECF}$$

can be converted to the actual cellular uptake rate constant $$K_{cell}^{Mn}$$

by division with $K_{ECF}$.

In this example, the cardiomyocyte cellular manganese uptake rate is hence, $$K_{cell}^{Mn} = 0.0691/0.72 = 0.096.$$

The determined value for the cardiomyocyte cellular manganese uptake rate is much higher than the rate constant calculated with the methods described in the prior art, this is because prior art methods do not correct for the effect of a lower manganese concentration in the ECF than in plasma.

Another implication of the correlation in time between plasma and the ECF, is that the data can be analysed with multiple linear regression without the time normalization and conversion to a straight line obtained by dividing the data with ΔR1plasma. Thus, solving the equation $$\Delta R1myocardium(t) = K_{ECF} * ECV * \Delta R1plasma + K_{cell}^{MN} * K_{ECF} * (1 - ECV)\int_0^t \Delta R1plasma(t)dt$$

With ΔR1myocardium(t) as the dependent variable and ΔR1plasma and $$(1 - ECV)\int_0^t \Delta R1\text{plasma}(t)dt$$

as two independent variables.

Given the data from FIG. 10, the solution is $$\Delta R1myocardium(t) = 0.2326 * \Delta R1plasma + 0{,}0687 * (1 - ECV)\int_0^t \Delta R1plasma(t)dt$$

The constants in this solution are less than 1% different from the methods using linearization of data and estimation of $K_{ECF}$. One significant advantage of using multiple linear regression is to avoid the division with ΔR1plasma and potential division by zero errors and inaccurate results when ΔR1plasma is small.

The invention claimed is:

1. A method for determining a cardiomyocyte cellular manganese uptake rate of a subject, the method comprising the steps of:

i) performing, at a time point $t_i$=0, a first longitudinal relaxation time measurement $T1_{blood}(0)$ of the blood of the subject, and performing, for a section of the heart of the subject, a first longitudinal relaxation time measurement $T1_{myocardium}(0)$ of the myocardium of the subject;

ii) administering to the subject a dose $d_a$ of a contrast agent at a dosing rate of $D_a$ μmol/kg/min, wherein the contrast agent comprises a manganese contrast agent having a stability constant of 10-18, or a pharmaceutically acceptable salt thereof, and wherein the administration is completed at a time $t_a$;

iii) performing, at one or more time points $t_i$ during the administration in step ii), 0-5 minutes before $t_a$, measurements $T1_{blood}(t_i)$ of the longitudinal relaxation time of the blood of the subject, and performing, for said section of the heart of the subject, at the same time points $t_i$, measurements $T1_{myocardium}(t_i)$ of the longitudinal relaxation time of the myocardium of the subject;

iv) performing, at one or more time points $t_i$ 0-60 minutes after $t_a$, measurements $T1_{blood}(t_i)$ of the longitudinal relaxation time of the blood of the subject and, for said section of the heart of the subject, at the same time points $t_i$, measurements $T1_{myocardium}(t_i)$ of the longitudinal relaxation time of the myocardium of the subject;

v) calculating the change in myocardial relaxation rate $\Delta R1_{myocard}(t_i)$ for each of the time points $t_i$ of steps i), iii) and iv) according to the formula $$\Delta R1_{myocard}(t_i) = \frac{1}{T1_{myocard}(t_i)} - \frac{1}{T1_{myocard}(0)};$$

vi) obtaining a haematocrit value hct for the subject;

vii) calculating the change in plasma relaxation rate $\Delta R1_{plasma}(t_i)$ for each of the time points $t_i$ of steps i), iii) and iv) according to the formula $$\Delta R1_{plasma}(t_i) = \frac{\frac{1}{T1_{blood}(t_i)} - \frac{1}{T1_{blood}(0)}}{1 - hct};$$

viii) estimating the integrals $$\int_0^{t_i} \Delta R1_{plasma}(t)dt$$

using each of the $\Delta R1_{plasma}(t_i)$ values of step vii);

ix) obtaining an estimate of an extracellular volume fraction (ECV) for said section of the heart of the subject;

x) defining an equation for a straight line y=A+Bx, wherein $$y = \frac{\Delta\text{R1myocardium}(t)}{\Delta R1\text{plasma}(t)},$$

$A=K_{ECF}*ECV$, wherein $K_{ECF}$ is a constant, $$B = K_{cell}^{\Delta R1} * K_{ECF}$$

and $$x = \frac{(1 - ECV) * \int_0^t \Delta R1\text{plasma}(t)dt}{\Delta R1\text{plasma}(t)};$$

and xi) estimating the slope B, and thus the cardiomyocyte cellular manganese uptake rate $$K_{cell}^{Mn} * K_{ECF} = B,$$

by a linear regression method with forced intercept $A=K_{ECF}*ECV$.

2. The method according to claim 1, wherein step vi) comprises measuring the haematocrit in the blood of the subject.

3. The method according to claim 1, wherein the contrast agent has a stability constant of 11-17.

4. The method according to claim 3, wherein the contrast agent has a stability constant of 14-16.

5. The method according to claim 1, wherein $K_{ECF}=1$.

6. The method according to claim 1, wherein in step ix) the ECV value is obtained by measuring pre- and 20 minutes post-contrast myocardial T1 after injection of a gadolinium contrast agent corrected for blood-pool T1 and serum haematocrit, performed 1-30 days before or 1-30 days after steps i)-iv).

7. A computer-implemented method of determining a cardiomyocyte cellular manganese uptake rate in a subject, comprising:

i) receiving from a PACS system of an MRI instrument scan data from a first longitudinal relaxation time measurement $T1_{blood}(0)$ of blood of the subject and data from a first longitudinal relaxation time measurement $T1_{myocardium}(0)$ of the myocardium of the subject, performed for a section of the heart of the subject;

ii) receiving from the PACS system of the MRI instrument series of scan data from one or more measurements $T1_{blood}(t_i)$ of the longitudinal relaxation time of the blood of the subject and one or more measurements $T1_{myocardium}(t_i)$ of the longitudinal relaxation time of the myocardium of the subject, performed for said section of the heart of the subject, wherein the $T1_{blood}(t_i)$ measurements and the $T1_{myocardium}(t_i)$ measurements have been performed at one or more time points $t_i$ during administration to the subject of a dose $d_a$ of a contrast agent at a dosing rate of $D_a$ µmol/kg/min, the contrast agent comprising a manganese contrast agent having a stability constant of 10-18, or a pharmaceutically acceptable salt thereof, the administration being completed at a time $t_a$, iii) receiving from the PACS system of the MRI instrument pulse sequence series data from one or more measurements $T1_{blood}(t_i)$ of the longitudinal relaxation time of the blood of the subject and from one or more measurements $T1_{myocardium}(t_i)$ of the longitudinal relaxation time of the myocardium of the subject, performed for said section of the heart of the subject, wherein the measurements have been performed at one or more time points $t_i$ up to 60 minutes after $t_a$;

iv) calculating the change in myocardial relaxation rate $\Delta R1_{myocard}(t_i)$ for each of the time points $t_i$ of steps i), ii) and iii) according to the formula $$\Delta R1_{myocard}(t_i) = \frac{1}{T1_{myocard(t_i)}} - \frac{1}{T1_{myocard}(0)};$$

v) receiving a haematocrit value, hct, for the subject;

vi) calculating the change in plasma relaxation rate $\Delta R1_{plasma}(t_i)$ for each of the time points $t_i$ of steps i), ii) and iii) according to the formula $$\Delta R1_{plasma}(t_i) = \frac{\frac{1}{T1_{blood}(t_i)} - \frac{1}{T1_{blood}(0)}}{1 - hct};$$

vii) estimating the integrals $$\int_0^{t_i} \Delta R1_{plasma}(t)dt$$

using each $\Delta R1_{plasma}(t_i)$ value of step vi);

viii) receiving an estimate of an extracellular volume fraction (ECV) for said section of the heart of the subject;

ix) defining an equation for a straight line $y=A+Bx$, wherein $$y = \frac{\Delta R1\text{myocardium}(t)}{\Delta R1\text{plasma}(t)},$$

$A=K_{ECF}*ECV$, wherein $K_{ECF}$ is a constant, $$B = K_{cell}^{\Delta R1} * K_{ECF}$$

and $$x = \frac{(1 - ECV) * \int_0^t \Delta R1\text{plasma}(t)dt}{\Delta R1\text{plasma}(t)};$$

and x) estimating the slope B, and thus the cardiomyocyte cellular manganese uptake rate $$K_{cell}^{Mn} * K_{ECF} = B,$$

by a linear regression method with forced intercept $A=K_{ECF}*ECV$.

8. A data processing apparatus comprising one or more processors and a memory storing instructions to perform the method of claim 7.

9. A computer program comprising instructions which, when the program is executed by a computer, cause the computer to carry out the method of claim 7.

10. A non-transitory computer-readable medium having stored thereupon the computer program of claim 9.

11. A method for in vivo diagnosis of heart failure or heart disease in a subject, comprising:

i) performing, at a time point $t_i=0$, a first longitudinal relaxation time measurement $T1_{blood}(0)$ of the blood of the subject, and performing, for a section of the heart of the subject, a first longitudinal relaxation time measurement $T1_{myocardium}(0)$ of the myocardium of the subject;

ii) administering to the subject a dose $d_a$ of a contrast agent at a dosing rate of $D_a$ µmol/kg/min, wherein the contrast agent comprises a manganese contrast agent having a stability constant of 10-18, or a pharmaceutically acceptable salt thereof, and wherein the administration is completed at a time $t_a$;

iii) performing, at one or more time points $t_i$ during the administration in step ii), 0-5 minutes before $t_a$, measurements $T1_{blood}(t_i)$ of the longitudinal relaxation time of the blood of the subject, and performing, for said section of the heart of the subject, at the same time points $t_i$, measurements $T1_{myocardium}(t_i)$ of the longitudinal relaxation time of the myocardium of the subject;

iv) performing, at one or more time points $t_i$ 0-60 minutes after $t_a$, measurements $T1_{blood}(t_i)$ of the longitudinal relaxation time of the blood of the subject and, for said section of the heart of the subject, at the same time points $t_i$, measurements $T1_{myocardium}(t_i)$ of the longitudinal relaxation time of the myocardium of the subject;

v) calculating the change in myocardial relaxation rate $\Delta R1_{myocard}(t_i)$ for each of the time points $t_i$ of steps i), iii) and iv) according to the formula $$\Delta R1_{myocard}(t_i) = \frac{1}{T1_{myocard(t_i)}} - \frac{1}{T1_{myocard}(0)};$$

vi) obtaining a haematocrit value hct for the subject;

vii) calculating the change in plasma relaxation rate $\Delta R1_{plasma}(t_i)$ for each of the time points $t_i$ of steps i), iii) and iv) according to the formula $$\Delta R1_{plasma}(t_i) = \frac{\frac{1}{T1_{blood}(t_i)} - \frac{1}{T1_{blood}(0)}}{1 - hct};$$

viii) estimating the integrals $$\int_0^{t_i} \Delta R1_{plasma}(t)dt$$

using each of the $\Delta R1_{plasma}(t_i)$ values of step vii);

ix) obtaining an estimate of an extracellular volume fraction (ECV) for said section of the heart of the subject;

x) defining an equation for a straight line y=A+Bx, wherein $$y = \frac{\Delta R1\text{myocardium}(t)}{\Delta R1\text{plasma}(t)},$$

A=$K_{ECF}$*ECV, wherein $K_{ECF}$ is a constant, $$B = K_{cell}^{\Delta R1} * K_{ECF}$$

and $$x = \frac{(1 - ECV) * \int_0^t \Delta R1\text{plasma}(t)dt}{\Delta R1\text{plasma}(t)};$$

and xi) estimating the slope B, and thus the cardiomyocyte cellular manganese uptake rate $$K_{cell}^{Mn} * K_{ECF} = B,$$

by a linear regression method with forced intercept A=$K_{ECF}$*ECV; and xii) comparing the $$K_{cell}^{Mn}$$

value to one or more reference values for the relaxivity change in order to diagnose a heart disease in the subject.

12. The method of claim 11, wherein step vi) comprises measuring the haematocrit in the blood of the subject.

13. The method of claim 11, wherein the contrast agent has a stability constant of 11-17.

14. The method of claim 11, wherein in step ix) the ECV value is obtained by measuring pre- and 20 minutes post-contrast myocardial T1 after injection of a gadolinium contrast agent corrected for blood-pool T1 and serum haematocrit, performed 1-30 days before or 1-30 days after steps i)-iv).

15. The method of claim 11, wherein the heart disease is heart failure with preserved ejection fraction, heart failure with reduced ejection fraction, dilated cardiomyopathy, hypertrophic cardiomyopathy, diabetic cardiomyopathy, hypertensive cardiomyopathy, and/or tako-tsubo cardiomyopathy.

16. The method of claim 11, wherein the contrast agent is MnDPDP.

17. The method of claim 13, wherein the contrast agent has a stability constant of 14-16.

* * * * *